US012583895B2

(12) United States Patent
Cheung-Flynn et al.

(10) Patent No.: US 12,583,895 B2
(45) Date of Patent: Mar. 24, 2026

(54) POLYPEPTIDES FOR RESTORING ENDOTHELIAL FUNCTION AND METHODS OF USE THEREOF

(71) Applicant: Vanderbilt University, Nashville, TN (US)

(72) Inventors: Joyce Cheung-Flynn, Nashville, TN (US); Colleen M. Brophy, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1162 days.

(21) Appl. No.: 17/430,365

(22) PCT Filed: Feb. 12, 2020

(86) PCT No.: PCT/US2020/017842
§ 371 (c)(1),
(2) Date: Aug. 12, 2021

(87) PCT Pub. No.: WO2020/167894
PCT Pub. Date: Aug. 20, 2020

(65) Prior Publication Data
US 2022/0127313 A1      Apr. 28, 2022

Related U.S. Application Data

(60) Provisional application No. 62/804,339, filed on Feb. 12, 2019.

(51) Int. Cl.
*C07K 14/47* (2006.01)
*A61K 38/00* (2006.01)
*A61P 9/00* (2006.01)

(52) U.S. Cl.
CPC ............ *C07K 14/4702* (2013.01); *A61P 9/00* (2018.01); *A61K 38/00* (2013.01)

(58) Field of Classification Search
None
See application file for complete search history.

(56) References Cited

U.S. PATENT DOCUMENTS 6,309,863 B1      10/2001   Anderson et al.
2003/0060399 A1*   3/2003   Brophy ..................... A61P 9/14
                                                                      435/325

2010/0291096 A1    11/2010   Schroeder
2012/0238508 A1*    9/2012   Brophy .................. C07K 14/00
                                                                      514/21.3
2016/0038576 A1     2/2016   Vasserot et al.
2017/0326215 A1    11/2017   Mahr et al.

FOREIGN PATENT DOCUMENTS

WO        2017/189826        11/2017

OTHER PUBLICATIONS

Xu and Wick, Molecular Medicine Today, Sep. 1996, 372-379 (Year: 1996).*
Evora, International Journal of Cardiology 73 (2000) 289-292 (Year: 2000).*
Milletti, Drug Discovery Today, vol. 17, Nos. 15/16, Aug. 2012, 850-860 (Year: 2012).*
DePorter, Chemistry & Biology 20, 434-444, Mar. 21, 2013 (Year: 2013).*
Manahan-Earley et al., Journal of Thrombosis and Haemostasis, 2014, 11 (Suppl. 1): 46-66 (Year: 2014).*
International Search Report and Written Opinion dated Jun. 23, 2020, from International Application No. PCT/US2020/017842, 12 pages.
Merrifield (1963, J. Am. Chem. Soc. 85: 2149-2154).
Carpino et al. (1972, J. Org. Chem. 37: 3403-3409).
Fields et al. 1990, Int. J. Pept. Protein Res. 35: 161-214.
Altschul, S. F. et al. (1990) J. Mol. Biol. 215, 403-410.
Green et al. Cell 55: 1179-1188, 1988.
Frankel et al. Cell 55: 1189-1193, 1988.
Fawell et al. Proc Natl Acad Sci USA 91: 664-668, 1994.
Schwarze et al. Science 285: 1569-1572, 1999.
Tyagi et al. J Biol Chem. 276: 3254-3261, 2001.
Ho et al. Cancer Res 61: 474-477, 2001.
Otaka et al., Tetrahedron Letters 36: 927-930 (1995).

* cited by examiner

*Primary Examiner* — Joseph Fischer
(74) *Attorney, Agent, or Firm* — Meunier Carlin & Curfman LLC

(57)      ABSTRACT

The present disclosure provides novel cell permeant polypeptides and pharmaceutical compositions thereof, and methods for using such polypeptides and pharmaceutical compositions for various therapeutic uses. The present disclosure more specifically provides polypeptides for restoring endothelial function.

6 Claims, 15 Drawing Sheets

Specification includes a Sequence Listing.

A
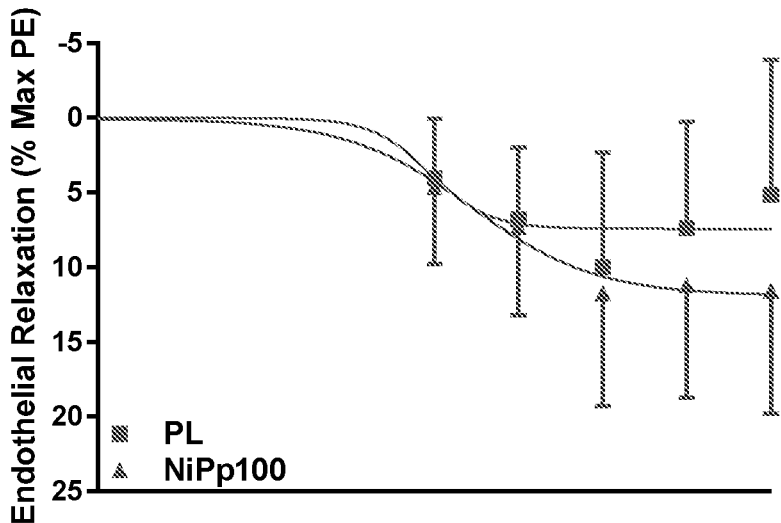
B
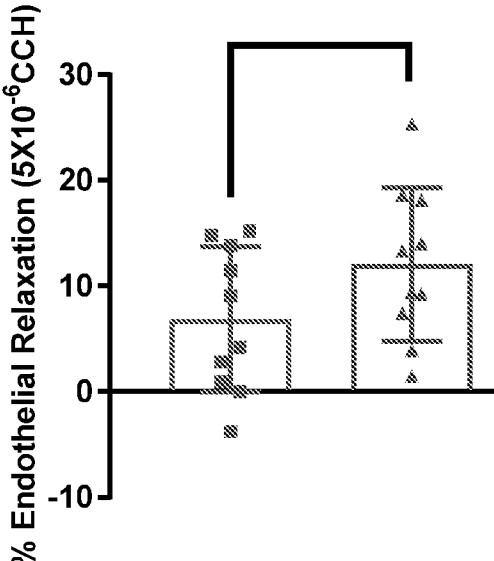
FIGS. 6A and B

A Polypeptides tested at 100μM

B Polypeptides tested at 500μM

A

| Kinases | % Inhibition | | |
| --- | --- | --- | --- |
| | NiPp | scr3NiPp | NiPp3 |
| MSK1 (RPS6KA5) | 66 | 32 | 91 |
| p38MAPKalpha | 61 | -6 | -4 |

B

A

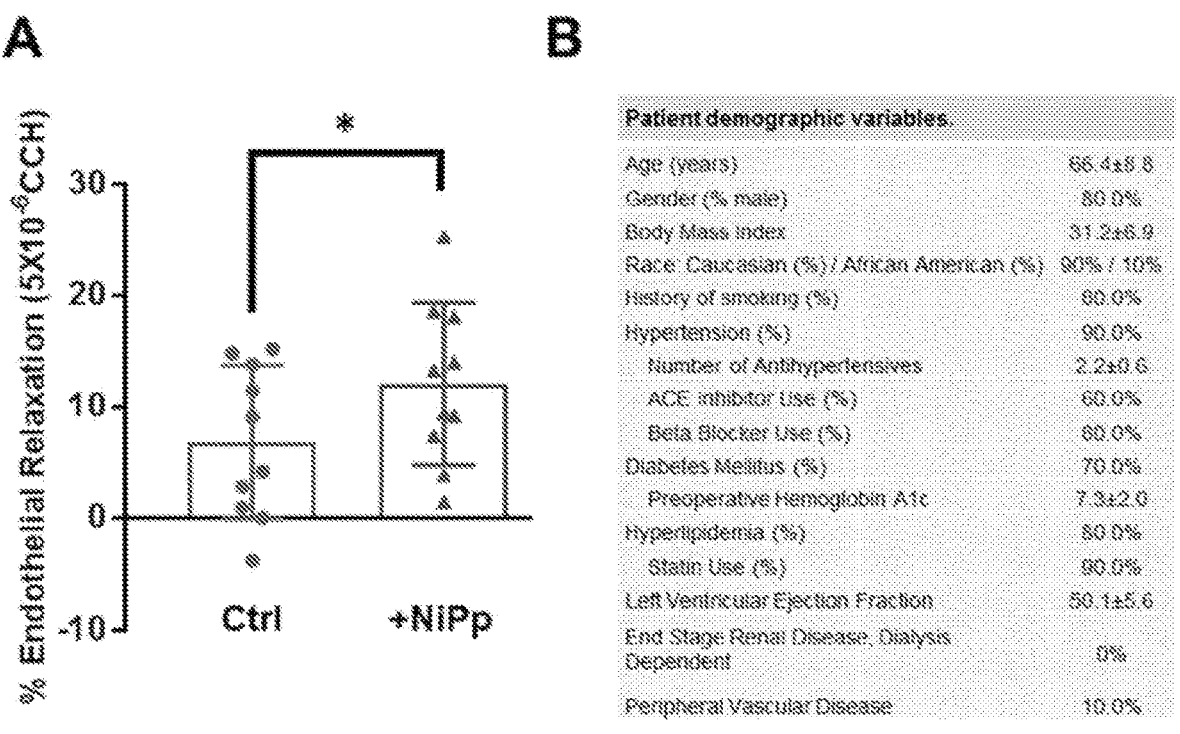

B

| Patient demographic variables. | |
|---|---|
| Age (years) | 66.4±8.8 |
| Gender (% male) | 80.0% |
| Body Mass Index | 31.2±6.9 |
| Race: Caucasian (%) / African American (%) | 90% / 10% |
| History of smoking (%) | 80.0% |
| Hypertension (%) | 90.0% |
| Number of Antihypertensives | 2.2±0.6 |
| ACE inhibitor Use (%) | 60.0% |
| Beta Blocker Use (%) | 60.0% |
| Diabetes Mellitus (%) | 70.0% |
| Preoperative Hemoglobin A1c | 7.3±2.0 |
| Hyperlipidemia (%) | 80.0% |
| Statin Use (%) | 90.0% |
| Left Ventricular Ejection Fraction | 50.1±5.6 |
| End Stage Renal Disease, Dialysis Dependent | 0% |
| Peripheral Vascular Disease | 10.0% |

FIGS. 17A and 17B

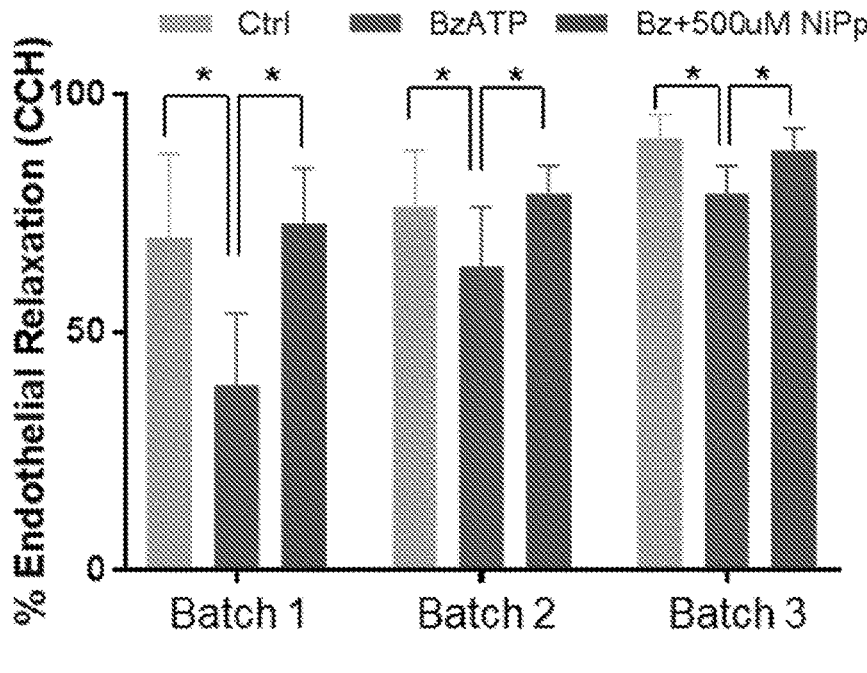

POLYPEPTIDES FOR RESTORING ENDOTHELIAL FUNCTION AND METHODS OF USE THEREOF

CROSS REFERENCE TO RELATED APPLICATIONS

This application is a U.S. National Stage of PCT/US2020/017842, filed Feb. 12, 2020, which claims the benefit of U.S. Provisional Patent Application Ser. No. 62/804,339, filed Feb. 12, 2019, the disclosures of which are expressly incorporated herein by reference.

STATEMENT REGARDING FEDERALLY SPONSORED RESEARCH

This invention was made with government support under grant numbers R01HL070715 and R01HL105731 awarded by the National Institutes of Health. The government has certain rights in the invention.

REFERENCE TO A SEQUENCE LISTING

This application contains a Sequence Listing in computer readable form, which is incorporated herein by reference.

FIELD

The invention is in the fields of cell and molecular biology, polypeptides, cellular repair, cellular regeneration, and therapeutic methods of use.

BACKGROUND

The endothelium is a fragile layer of cells that line blood vessels. Injury to the endothelium contributes to both acute (malperfusion, edema) and chronic (atherosclerosis, diabetes) pathology. The endothelium represents a model cell type to measure physiologic function in that when the endothelium is healthy, in response to acetylcholine, the cells release nitric oxide (NO) which leads to relaxation of the underlying smooth muscle. When the endothelium is injured (mechanical, chemical, oxidative, inflammatory) either acutely or chronically, endothelial function becomes impaired (endothelial dysfunction), NO production is decreased in response to injury, and there is less relaxation of smooth muscle.

Endothelial function also decreases with age. This may be due to chronic injury or failure of reparative or regenerative responses to injury. Injury leads to activation of stress activated signaling pathways, changes in gene expression, and a unique response in the endoplasmic reticulum (where protein manufacturing and processing occurs). Endoplasmic reticulum can be induced by the antibiotic tunicamycin, and treatment of the endothelium with tunicamycin leads to endothelial dysfunction. Injury also leads to release of ATP which causes endothelial dysfunction. ATP activates purinergic receptors (P2X7R) which subsequently lead to p38 MAPK activation. Activation of p38 MAPK is also associated with endothelial dysfunction. The antibiotic anisomycin activates p38MAPK, and treatment with anisomycin also causes endothelial dysfunction. p38MAPK is activated during inflammation by cytokines such as interleukin-1 beta (IL-1β), and treatment with IL-1β leads to endothelial dysfunction. What is needed are novel polypeptides that can be used for restoring endothelial function and for treating conditions and diseases where improved endothelial function is beneficial.

The compounds, compositions, and methods disclosed herein address these and other needs.

SUMMARY

Disclosed herein are polypeptides and compositions for restoring endothelial function. The inventors have identified novel, non-naturally occurring chimeric polypeptides that restore endothelial function after stretch injury and endoplasmic reticulum stress injury.

In some aspects, disclosed herein is a polypeptide comprising: an amino acid sequence according to the general formula X1-X2; wherein X1 comprises a transduction domain; and X2 comprises a polypeptide capable of restoring endothelial function; wherein X2 includes Z3; and wherein Z3 is selected from a phosphoserine or a phosphoserine analog.

In some embodiments, X1 is selected from GRKKRRQRRRPPQ (SEQ ID NO:3); AYARAAARQARA (SEQ ID NO:4); DAATATRGRSAASRPTERPRAPAR-SASRPRRPVE (SEQ ID NO:5); GWTLN-SAGYLLGLINLKALAALAKKIL (SEQ ID NO:6); PLS-SISRIGDP (SEQ ID NO:7); AAVALLPAVLLALLAP (SEQ ID NO:8); AAVLLPVLLAAP (SEQ ID NO:9); VTVLAL-GALAGVGVG (SEQ ID NO:10); GALFLGWL-GAAGSTMGAWSQP (SEQ ID NO:11); GWTLN-SAGYLLGLINLKALAALAKKIL (SEQ ID NO:12); KLALKLALKALKAALKLA (SEQ ID NO:13); KETWWETWWTEWSQPKKKRKV (SEQ ID NO:14); KAFAKLAARLYRKAGC (SEQ ID NO:15); KAFAK-LAARLYRAAGC (SEQ ID NO:16); AAFAKLAARLYRK-AGC (SEQ ID NO:17); KAFAALAARLYRKAGC (SEQ ID NO:18); KAFAKLAAQLYRKAGC (SEQ ID NO:19), AGGGGYGRKKRRQRRR (SEQ ID NO:20); YGRKKRRQRRR (SEQ ID NO:21); YARAAARQARA (SEQ ID NO:22); or LTVK (SEQ ID NO:23). In some embodiments, X1 comprises YARAAARQARA (SEQ ID NO:22).

In some embodiments, X2 is selected from SPAARRA (pS)AILPG (SEQ ID NO:24); SPARRA(pS)AILPG (SEQ ID NO:25); SPAARRV(pS)AILPG (SEQ ID NO:26); SPARRV(pS)AILPG (SEQ ID NO:27); SPAARGA(pS) AILPG (SEQ ID NO:28); SPARGA(pS)AILPG (SEQ ID NO:29); ARRA(pS)AILPG (SEQ ID NO:30); ARRV(pS) AILPG (SEQ ID NO:31); ARGA(pS)AILPG (SEQ ID NO:32); or SPARRA(pS)ALLPG (SEQ ID NO:74). In some embodiments, X2 comprises SPAARRA(pS)AILPG (SEQ ID NO:24).

In some embodiments, Z3 comprises a phosphoserine. In some embodiments, Z3 comprises a phosphoserine analog.

In some embodiments, the polypeptide comprises the amino acid sequence YARAAARQARASPAARRA(pS) AILPG (SEQ ID NO:1).

In some aspects, disclosed herein is a pharmaceutical composition comprising one or more polypeptides of the present invention and a pharmaceutically acceptable carrier.

The polypeptides and compositions disclosed herein comprise non-naturally occurring chimeric polypeptides for use as therapeutic agents for the following: (a) treating or preventing endothelial dysfunction; (b) preventing aging and the consequences of aging (for example, prolonging life (longevity)); (c) treating, preventing and/or reversing atherosclerosis, atherosclerotic lesions, and the consequences of atherosclerosis (myocardial infarction, heart failure, renal failure, stroke, peripheral vascular disease, amputation, death); (d) enhancing techniques for treating atherosclerotic lesions and preventing recurrence (re-stenosis) of atherosclerotic lesions; (e) treating or preventing cardiovascular complications of endothelial dysfunction (angina, myocardial infarction, stroke, death); (f) treating or preventing cardiovascular complications of endothelial dysfunction (angina, myocardial infarction, stroke, death) in patients with metabolic syndrome; (g) treating or preventing arterial stiffness and hypertension and the consequences of arterial stiffness and hypertension (stroke, heart failure); (h) treating or preventing failure of vascular conduits used as bypass grafts; (i) treating or preventing erectile dysfunction; (j) treating or preventing endothelial dysfunction (e.g., acute endothelial dysfunction) associated with injury, burn, acidosis, and/or sepsis and/or (k) to treat or preventing inflammatory diseases (for example, sepsis, rheumatoid arthritis, Crohn's disease, asthma, COPD), chronic pain, or cancer.

In some aspects, disclosed herein is a method for restoring endothelial function, comprising: administering to a subject in need thereof an effective amount of a polypeptide comprising:

an amino acid sequence according to the general formula X1-X2; wherein

X1 comprises a transduction domain; and

X2 comprises a polypeptide capable of restoring endothelial function;

wherein X2 includes Z3; and wherein Z3 is selected from a phosphoserine or a phosphoserine analog.

In some embodiments, the subject is a mammal. In some embodiments, the subject is a human.

In some aspects, disclosed herein is a method for preventing aging, comprising: administering to a subject in need thereof a therapeutically effective amount of a polypeptide comprising:

an amino acid sequence according to the general formula X1-X2; wherein

X1 comprises a transduction domain; and

X2 comprises a polypeptide capable of restoring endothelial function;

wherein X2 includes Z3; and wherein Z3 is selected from a phosphoserine or a phosphoserine analog.

In some aspects, disclosed herein is a method for restoring endothelial function, comprising: administering to a subject in need thereof an effective amount of a polypeptide comprising: an amino acid sequence according to the general formula X1-X2; wherein X1 comprises a transduction domain; and X2 is SPAARRA(pS)AILPG (SEQ ID NO:24);

wherein pS is phosphoserine.

In another aspect, the present invention provides isolated nucleic acid sequences encoding a polypeptide of the present invention. In further aspects, the present invention provides recombinant expression vectors comprising the nucleic acid sequences of the present invention, and host cells transfected with the recombinant expression vectors of the present invention.

BRIEF DESCRIPTION OF THE DRAWINGS

The accompanying figures, which are incorporated in and constitute a part of this specification, illustrate several aspects described below.

As seen in FIG. 1, endothelial function is lower in old rats.

As seen in FIG. 2, ATP injury led to decreased endothelial function that was restored by treatment with NiPp.

As seen in FIG. 3, stretch injury led to decreased endothelial function that was restored by treatment with NiPp.

As seen in FIG. 4, injury led to decreased endothelial function that was restored by treatment with NiPp.

As seen in FIG. 5, when normalized to baseline relaxation, NiPp led to 183±24% in relaxation responses in HSV.

FIGS. 6A and 6B show that polypeptide restores endothelial function in aged human saphenous veins. FIG. 6A shows human saphenous veins (HSV) were collected from patients undergoing coronary artery bypass grafting procedures (age=66.4±8.8) and treated with NiPp (100 μM) for 1 hour at room temperature. PE-precontracted tissues were treated with carbachol (CCH; $10^{-8}$ to $10^{-5}$M). Percent relaxation were determined as a change to the maximal PE-induced contraction. Data are reported as mean responses±standard deviation. n=10. FIG. 6B shows baseline endothelial function in HSV was low. Treatment with NiPp led to increased endothelial function in HSV. When normalized to baseline relaxation, NiPp led to 255±321.5% in relaxation responses in HSV.

FIG. 7A shows that percent relaxation induced by $5 \times 10^{-7}$M CCH was calculated. *p<0.05 in two-way ANOVA with Tukey post-tests. FIG. 7B shows that RA rings were snap frozen either untreated or immediately after treatment. Proteins were extracted and immunoblotted to examine p38MAPK phosphorylation. Quantification of relative phosphorylation to total p38MAPK level is shown. n=10, *p<0.05 in one-way ANOVA with Tukey post-test. NiPp restores endothelial dysfunction and reduced p38 MAPK phosphorylation induced by anisomycin in RA.

FIG. 8A shows that RA were either suspended in the muscle bath, contracted with PE and then treated with escalating doses of carbachol (CCH; $10^{-8}$ to $10^{-5}$ M). The percent relaxation was determined as a change to the maximal PE-induced contraction. n=5 rats; #p<0.05, two-way ANOVA. FIG. 8B shows that RA were snap-frozen after stretch injury and treatment with NiPp (500 μM) for 1 h, protein extracted and immunoblotted to examine P38MAPK phosphorylation. Quantification of relative phosphorylation to total p38MAPK level is shown. N=10. *p<0.05, in one-way ANOVA with Tukey post-test. NiPp restores endothelial dysfunction and reduced p38 MAPK phosphorylation induced by stretch injury in RA.

FIG. 14A shows top 2 candidates showing more than 60% inhibition by NiPp. FIG. 14B shows kinase dendrogram showing proportional circle to % inhibition using KinMap (www.kinhub.org). Differential inhibitory activities were demonstrated by the peptides. NiPp inhibits MSK1 and p38MAPK alpha by >60%. These two kinases are central to the p38MAPK kinase signaling cascade that play important roles in stress and inflammatory responses. NiPp-specific inhibitory activity to p38 MAPK were not detected for NiPp3 (non-phosphorylated) or scr3NiPp (scrambled) polypeptides.

FIG. 15A shows that RA were suspended in the muscle bath, contracted with PE and then relaxed with escalating doses of CCH ($10^{-8}$ to $10^{-5}$ M). The force generated was determined and was adjusted to the weight and length of the tissue. Representative tracings from 1 out of 6 different rats are shown. Orange arrow heads indicate addition of PE (orange) and CCH (blue). FIG. 15B shows that percent relaxation induced by $5\times10^{-7}$ M CCH was calculated. *$p<0.05$ in one-way ANOVA with Tukey post-test. FIG. 15C shows that RA rings were snap frozen either untreated or immediately after treatment. Proteins were extracted and phosphorylation of p38 MAPK was determined by Western blot analysis. Western blots shown are representative of 1 out of 10 rats. FIG. 15D shows quantification of relative phosphorylation to total p38 MAPK level. n=10, *$p<0.05$ in one-way ANOVA with Tukey post-test. Data are expressed as mean±SD.

FIG. 16A shows that freshly isolated rat aorta (RA) was cut into rings and then pretreated in the absence or presence of NiPp (500 μM) in PL for 30 min. Tissue rings were then transferred to NS and continued incubation in the absence or presence of NiPp (500 μM) for 2 h at room temperature. Control rings (Ctrl) were incubated in PL for 2.5 h. FIG. 16B shows that RA was either left untreated (Ctrl) or treated with BzATP (1 mM) in the absence of presence NiPp (500 μM) in PL for 1 h at room temperature. After treatments, RA were suspended in the muscle bath, contracted with PE and then treated with escalating doses of carbachol (CCH; $10^{-8}$ to $10^{-5}$M). The percent relaxation was determined as a change to the maximal PE-induced contraction. Percent relaxation to $5\times10^{-7}$ M CCH is shown. n=5-7 rats. *$p<0.05$ in one-way ANOVA with Tukey post-test. Data are expressed as mean±SD.

FIGS. 17A and 17B show that NiPp improves endothelial relaxation in human saphenous veins (HSV). FIG. 17A shows that HSV, collected from patients undergoing CABG immediately after surgical harvest, were either incubated in PL in the absence (Ctrl) or presence of NiPp (100 μM) for 2 h at room temperature. HSV were suspended in the muscle bath, contracted with PE and treated with carbachol (CCH; $10^{-8}$ to $10^{-5}$ M). The percent relaxation was determined as a change to the maximal PE-induced contraction. Percent relaxation to $5\times10^{-6}$ M CCH is shown. n=10; *$p<0.05$ in paired t-test. FIG. 17B shows patient demographic variables. Data are expressed as mean±SD.

FIG. 18 shows batch performance of NiPp. NiPp was synthesized at 3 separate times and tested in the muscle bath using rat aorta (RA). RA was either left untreated (Ctrl) or treated with BzATP (1 mM) in the absence of presence of NiPp (500 μM) in PL for 2 h at room temperature. After treatments, RA were suspended in the muscle bath, contracted with PE and then treated with escalating doses of carbachol $5\times10^{-7}$ M CCH. The percent relaxation was determined as a change to the maximal PE-induced contraction. The three batches displayed similar bioactivity. n=6 rats for each batch. *$p<0.05$ in one-way ANOVA with Tukey post-test. Data are expressed as mean±SD.

FIG. 19A shows candidates showing more than 40% inhibition by NiPp. FIG. 19B shows kinase dendrogram showing proportional circle to % inhibition using KinMap (www.kinhub.org). FIG. 19C shows the kinase interaction network of NiPp molecular targets in human. Interaction of candidate molecular targets of NiPp identified in the kinase profiling assays were predicted using the STRING system (string-db.org) based on interaction of different type. Five different interactions were revealed among 4 putative molecular targets of NiPp.

DETAILED DESCRIPTION

Figure 1:
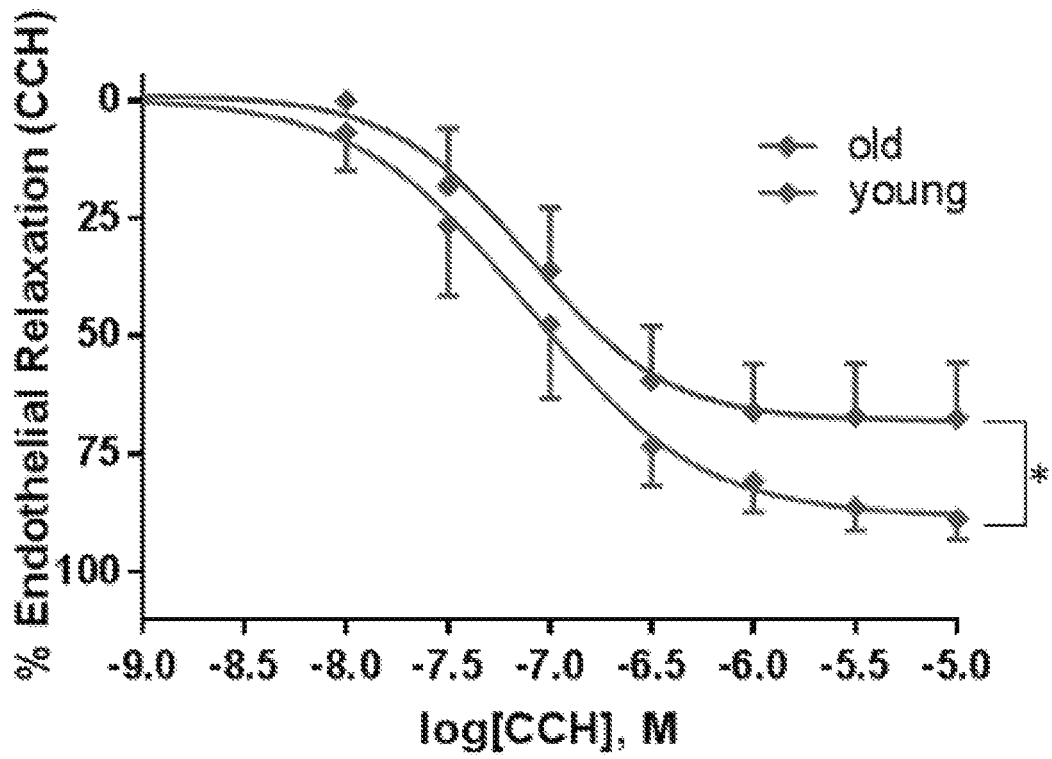
FIG. 1 shows that aging leads to decreased endothelial function in rodent blood vessels. Freshly isolated aorta from young (4 months) and old (20 months) rats were suspended in the muscle bath. To determine the effect of injury on endothelial function, phenylephrine (PE)-precontracted tissues were treated with carbachol (CCH; $5\times10^{-7}$M) and the percent relaxation was determined as a change to the maximal PE-induced contraction. Data are reported as mean responses±standard deviation. n=7-8. *p<0.05, two-way ANOVA.

Disclosed herein are polypeptides and compositions for restoring endothelial function. The inventors have identified novel, non-naturally occurring chimeric polypeptides that restore endothelial function after stretch injury and endoplasmic reticulum stress injury.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

The single letter designation for amino acids is used predominately herein. As is well known by one of skill in the art, such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The term "polypeptide" or "protein" is used in its broadest sense to refer to a sequence of subunit amino acids, amino acid analogs, or peptidomimetics. The subunits are linked by peptide bonds, except where noted. The polypeptides described herein may be chemically synthesized or recombinantly expressed. In some embodiments, the polypeptides of the present invention are chemically synthesized. Synthetic polypeptides, prepared using the known techniques of solid phase, liquid phase, or peptide condensation techniques, or any combination thereof, can include natural and unnatural amino acids Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85: 2149-2154), or the base-labile N-α-amino protected 9-fluorenylmethoxycarbonyl (Fmoc) amino acids first described by Carpino and Han (1972, J. Org. Chem. 37: 3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35: 161-214, or using automated synthesizers. The polypeptides disclosed herein may comprise D-amino acids (which are resistant to L-amino acid-specific proteases in vivo), a combination of D- and L-amino acids, and various "designer" amino acids (e.g. β-methyl amino acids, C-α-methyl amino acids, and N-α-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a polypeptide would be resistant to protease activity and would possess an extended half-live in vivo.

Conservative substitutions of amino acids in proteins and polypeptides are known in the art. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substantial changes in protein function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

A "derivative" of a protein or peptide can contain post-translational modifications (such as covalently linked carbohydrate), depending on the necessity of such modifications for the performance of a specific function.

The "fragments," whether attached to other sequences or not, can include insertions, deletions, substitutions, or other selected modifications of particular regions or specific amino acids residues, provided the activity of the fragment is not significantly altered or impaired compared to the nonmodified peptide or protein. These modifications can provide for some additional property, such as to remove or add amino acids capable of disulfide bonding, to increase its bio-longevity, to alter its secretory characteristics, etc. In any case, the fragment possesses a bioactive property (for example, restoring endothelial function).

A "variant" refers to a molecule substantially similar in structure and immunoreactivity. Thus, provided that two molecules possess a common immunoactivity and can substitute for each other, they are considered "variants" as that term is used herein even if the composition or secondary, tertiary, or quaternary structure of one of the molecules is not identical to that found in the other, or if the amino acid or nucleotide sequence is not identical. Thus, in one embodiment, a variant refers to a protein whose amino acid sequence is similar to a reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 30%, 40%, 50%, 60%, 70%, 75%, 80%, 85%, 90%, or 95% identical to the reference sequence. For example, variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using any available sequence alignment program. An example includes the MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) J. Mol. Biol. 215, 403-410. Identities are calculated by the Align program (DNAstar, Inc.) In all cases, internal gaps and amino acid insertions in the candidate sequence as aligned are not ignored when making the identity calculation.

As used herein, the term "capable of restoring endothelial function" refers to agents (for example, polypeptides) that can improve the functioning of endothelial cells, or improve the symptoms associated with defects in endothelial function. In one assay for measuring endothelial function, for example, phenylephrine (PE)-precontracted tissues are treated with carbachol (CCH; with a concentration including, for example, $10^{-8}$ to $10^{-5}$M) and the percent relaxation is determined as a change to the maximal PE-induced contraction. In some embodiments, the improvement in restoring endothelial function after injury (for example, stretch injury or endoplasmic reticulum stress injury) can be at least 5% (for example, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, or more) greater than the endothelial function observed in a comparable injury control. In some embodiments, endothelial function can be restored to about 50%, about 60%, about 70%, about 80%, about 90%, about 100%, or more, of the endothelial function of a healthy control (for example, wild-type endothelial function).

The term "about" as used herein when referring to a measurable value such as an amount, a percentage, and the like, is meant to encompass variations of ±20%, ±10%, ±5%, or ±1% from the measurable value.

Nucleic Acids and Polypeptides

In some aspects, disclosed herein is a polypeptide comprising:

an amino acid sequence according to the general formula X1-X2; wherein

X1 comprises a transduction domain; and

X2 comprises a polypeptide capable of restoring endothelial function;

wherein X2 includes Z3; and wherein Z3 is selected from a phosphoserine or a phosphoserine analog.

In some embodiments, X1 comprises a transduction domain. As used herein, the term "transduction domain" means one or more amino acid sequence or any other molecule that can carry the active domain across cell membranes. These domains can be linked to other polypeptides to direct movement of the linked polypeptide across cell membranes. In some embodiments, the transducing molecules can be covalently linked to the active polypeptide. In some cases, the transducing molecules do not need to be covalently linked to the active polypeptide. In some embodiments, the transduction domain is linked to the rest of the polypeptide via peptide bonding. (See, for example, Cell 55: 1179-1188, 1988; Cell 55: 1189-1193, 1988; Proc Natl Acad Sci USA 91: 664-668, 1994; Science 285: 1569-1572, 1999; J Biol Chem. 276: 3254-3261, 2001; and Cancer Res 61: 474-477, 2001). In some embodiments, any of the polypeptides as described herein would include at least one transduction domain. In a further embodiment, X1 comprises one or more transduction domains.

In some embodiments, X1 is selected from GRKKRRQRRRPPQ (SEQ ID NO:3); AYARAAARQARA (SEQ ID NO:4); DAATATRGRSAASRPTERPRAPARSASRPRRPVE (SEQ ID NO:5); GWTLNSAGYLLGLINLKALAALAKKIL (SEQ ID NO:6); PLSSISRIGDP (SEQ ID NO:7); AAVALLPAVLLALLAP (SEQ ID NO:8); AAVLLPVLLAAP (SEQ ID NO:9); VTVLALGALAGVGVG (SEQ ID NO:10); GALFLGWLGAAGSTMGAWSQP (SEQ ID NO:11); GWTLNSAGYLLGLINLKALAALAKKIL (SEQ ID NO:12); KLALKLALKALKAALKLA (SEQ ID NO:13); KETWWETWWTEWSQPKKKRKV (SEQ ID NO:14); KAFAKLAARLYRKAGC (SEQ ID NO:15); KAFAK- LAARLYRAAGC (SEQ ID NO:16); AAFAKLAARLYRKAGC (SEQ ID NO:17); KAFAALAARLYRKAGC (SEQ ID NO:18); KAFAKLAAQLYRKAGC (SEQ ID NO:19); AGGGGYGRKKRRQRRR (SEQ ID NO:20); YGRKKRRQRRR (SEQ ID NO:21); YARAAARQARA (SEQ ID NO:22); LTVK (SEQ ID NO:23); or a fragment, variant, or derivative thereof.

In some embodiments, X1 comprises GRKKRRQRRRPPQ (SEQ ID NO:3). In some embodiments, X1 comprises AYARAAARQARA (SEQ ID NO:4). In some embodiments, X1 comprises DAATATRGRSAASRPTERPRAPARSASRPRRPVE (SEQ ID NO:5). In some embodiments, X1 comprises GWTLNSAGYLLGLINLKALAALAKKIL (SEQ ID NO:6). In some embodiments, X1 comprises PLSSISRIGDP (SEQ ID NO:7). In some embodiments, X1 comprises AAVALLPAVLLALLAP (SEQ ID NO:8). In some embodiments, X1 comprises AAVLLPVLLAAP (SEQ ID NO:9). In some embodiments, X1 comprises VTVLALGALAGVGVG (SEQ ID NO:10). In some embodiments, X1 comprises GALFLGWLGAAGSTMGAWSQP (SEQ ID NO:11). In some embodiments, X1 comprises GWTLNSAGYLLGLINLKALAALAKKIL (SEQ ID NO:12). In some embodiments, X1 comprises KLALKLALKALKAALKLA (SEQ ID NO:13). In some embodiments, X1 comprises KETWWETWWTEWSQPKKKRKV (SEQ ID NO:14). In some embodiments, X1 comprises KAFAKLAARLYRKAGC (SEQ ID NO:15). In some embodiments, X1 comprises KAFAKLAARLYRAAGC (SEQ ID NO:16). In some embodiments, X1 comprises AAFAKLAARLYRKAGC (SEQ ID NO:17). In some embodiments, X1 comprises KAFAALAARLYRKAGC (SEQ ID NO:18). In some embodiments, X1 comprises KAFAKLAAQLYRKAGC (SEQ ID NO:19). In some embodiments, X1 comprises AGGGGYGRKKRRQRRR (SEQ ID NO:20). In some embodiments, X1 comprises YGRKKRRQRRR (SEQ ID NO:21). In some embodiments, X1 comprises YARAAARQARA (SEQ ID NO:22). In some embodiments, X1 comprises LTVK (SEQ ID NO:23).

In some embodiments, X1 comprises a sequence that is at least 60% (for example, at least 60%, at least 65%, at least 70%, at least 75%, at least 80%, at least 85%, at least 90%, at least 95%) identical to an amino acid sequence selected from GRKKRRQRRRPPQ (SEQ ID NO:3); AYARAAARQARA (SEQ ID NO:4); DAATATRGRSAASRPTERPRAPARSASRPRRPVE (SEQ ID NO:5); GWTLNSAGYLLGLINLKALAALAKKIL (SEQ ID NO:6); PLSSISRIGDP (SEQ ID NO:7); AAVALLPAVLLALLAP (SEQ ID NO:8); AAVLLPVLLAAP (SEQ ID NO:9); VTVLALGALAGVGVG (SEQ ID NO:10); GALFLGWLGAAGSTMGAWSQP (SEQ ID NO:11); GWTLNSAGYLLGLINLKALAALAKKIL (SEQ ID NO:12); KLALKLALKALKAALKLA (SEQ ID NO:13); KETWWETWWTEWSQPKKKRKV (SEQ ID NO:14); KAFAKLAARLYRKAGC (SEQ ID NO:15); KAFAKLAARLYRAAGC (SEQ ID NO:16); AAFAKLAARLYRKAGC (SEQ ID NO:17); KAFAALAARLYRKAGC (SEQ ID NO:18); KAFAKLAAQLYRKAGC (SEQ ID NO:19), AGGGGYGRKKRRQRRR (SEQ ID NO:20); YGRKKRRQRRR (SEQ ID NO:21); YARAAARQARA (SEQ ID NO:22); and LTVK (SEQ ID NO:23).

Niban (also known as FAM129A) is phosphoprotein involved in apoptosis, cancer, and the endothelial response to stress. Niban phosphorylation decreases in vascular tissues after injury. The inventors have identified certain portions of the Niban protein that are capable of restoring endothelial function. For example, the inventors have identified novel, non-naturally occurring chimeric polypeptides that restore endothelial function after stretch injury and endoplasmic reticulum stress injury.

In some embodiments, the X2 portion of the chimeric polypeptide comprises a fragment of Niban (or a variant thereof).

In some embodiments, the X2 portion of the chimeric polypeptide comprises a Niban (or FAM129A) homolog. In some embodiments, the X2 sequence can be from a mammal, for example, human, rat, mouse, etc.

In some embodiments, X2 is selected from SPAARRA (pS)AILPG (SEQ ID NO:24); SPARRA(pS)AILPG (SEQ ID NO:25); SPAARRV(pS)AILPG (SEQ ID NO:26); SPARRV(pS)AILPG (SEQ ID NO:27); SPAARGA(pS) AILPG (SEQ ID NO:28); SPARGA(pS)AILPG (SEQ ID NO:29); ARRA(pS)AILPG (SEQ ID NO:30); ARRV(pS) AILPG (SEQ ID NO:31); ARGA(pS)AILPG (SEQ ID NO:32); or SPARRA(pS)ALLPG (SEQ ID NO:74); or a fragment, variant, or derivative thereof.

In some embodiments, X2 comprises SPAARRA(pS) AILPG (SEQ ID NO:24). In some embodiments, X2 comprises SPARRA(pS)AILPG (SEQ ID NO:25). In some embodiments, X2 comprises SPAARRV(pS)AILPG (SEQ ID NO:26). In some embodiments, X2 comprises SPARRV (pS)AILPG (SEQ ID NO:27). In some embodiments, X2 comprises SPAARGA(pS)AILPG (SEQ ID NO:28). In some embodiments, X2 comprises SPARGA(pS)AILPG (SEQ ID NO:29). In some embodiments, X2 comprises ARRA(pS)AILPG (SEQ ID NO:30). In some embodiments, X2 comprises ARRV(pS)AILPG (SEQ ID NO:31). In some embodiments, X2 comprises ARGA(pS)AILPG (SEQ ID NO:32). In some embodiments, X2 comprises SPARRA(pS) ALLPG (SEQ ID NO:74).

In some embodiments, X2 comprises a sequence that is at least 60% (for example, at least 60%, at least 65%, at least 70%, at least 75%, at least 80%, at least 85%, at least 90%, at least 95%) identical to an amino acid sequence selected from SPAARRA(pS)AILPG (SEQ ID NO:24); SPARRA (pS)AILPG (SEQ ID NO:25); SPAARRV(pS)AILPG (SEQ ID NO:26); SPARRV(pS)AILPG (SEQ ID NO:27); SPAARGA(pS)AILPG (SEQ ID NO:28); SPARGA(pS) AILPG (SEQ ID NO:29); ARRA(pS)AILPG (SEQ ID NO:30); ARRV(pS)AILPG (SEQ ID NO:31); ARGA(pS) AILPG (SEQ ID NO:32); or SPARRA(pS)ALLPG (SEQ ID NO:74).

In some embodiments, the polypeptide is selected from

```
                              (SEQ ID NO: 33)
GRKKRRQRRRPPQSPAARRA(pS)AILPG;

(SEQ ID NO: 34)
AYARAAARQARASPAARRA(pS)AILPG;

(SEQ ID NO: 35)
DAATATRGRSAASRPTERPRAPARSASRPRRPVESPAARRA(pS)AILPG;

(SEQ ID NO: 36)
GWTLNSAGYLLGLINLKALAALAKKILSPAARRA(pS)AILPG;

(SEQ ID NO: 37)
PLSSISRIGDPSPAARRA(pS)AILPG;

(SEQ ID NO: 38)
AAVALLPAVLLALLAPSPAARRA(pS)AILPG;

(SEQ ID NO: 39)
AAVLLPVLLAAPSPAARRA(pS)AILPG;

(SEQ ID NO: 40)
VTVLALGALAGVGVGSPAARRA(pS)AILPG;
```

-continued
```
                              (SEQ ID NO: 41)
GALFLGWLGAAGSTMGAWSQPSPAARRA(pS)AILPG;

(SEQ ID NO: 42)
GWTLNSAGYLLGLINLKALAALAKKILSPAARRA(pS)AILPG;

(SEQ ID NO: 43)
KLALKLALKALKAALKLASPAARRA(pS)AILPG;

(SEQ ID NO: 44)
KETWWETWWTEWSQPKKKRKVSPAARRA(pS)AILPG;

(SEQ ID NO: 45)
KAFAKLAARLYRKAGCSPAARRA(pS)AILPG;

(SEQ ID NO: 46)
KAFAKLAARLYRAAGCSPAARRA(pS)AILPG;

(SEQ ID NO: 47)
AAFAKLAARLYRKAGCSPAARRA(pS)AILPG;

(SEQ ID NO: 48)
KAFAALAARLYRKAGCSPAARRA(pS)AILPG;

(SEQ ID NO: 49)
KAFAKLAAQLYRKAGCSPAARRA(pS)AILPG, (SEQ ID NO: 50)
AGGGGYGRKKRRQRRRSPAARRA(pS)AILPG;

(SEQ ID NO: 51)
YGRKKRRQRRRSPAARRA(pS)AILPG;

(SEQ ID NO: 1)
YARAAARQARASPAARRA(pS)AILPG;
or (SEQ ID NO: 52)
LTVKSPAARRA(pS)AILPG.
```

In some embodiments, the polypeptide comprises the amino acid sequence YARAAARQARASPAARRA(pS) AILPG (SEQ ID NO:1).

In some embodiments, any of the X1 transduction domains (for example, SEQ ID NOs:3 to 23) can be used in combination with any of the X2 polypeptides (for example, SEQ ID NOs:24 to 32, or 74).

In some aspects, the X1 and X2 polypeptide sequences can be reversed. Thus, in some aspects, disclosed herein is a polypeptide comprising:

an amino acid sequence according to the general for hula X2-X1; wherein

X1 comprises a transduction domain; and

X2 comprises a polypeptide capable of restoring endothelial function;

wherein X2 includes Z3; and wherein Z3 is selected from a phosphoserine or a phosphoserine analog.

In some embodiments, the polypeptide comprises a sequence that is at least 60% (for example, at least 60%, at least 65%, at least 70%, at least 75%, at least 80%, at least 85%, at least 90%, at least 95%) identical to an amino acid sequence selected from

```
                              (SEQ ID NO: 33)
GRKKRRQRRRPPQSPAARRA(pS)AILPG;

(SEQ ID NO: 34)
AYARAAARQARASPAARRA(pS)AILPG;

(SEQ ID NO: 35)
DAATATRGRSAASRPTERPRAPARSASRPRRPVESPAARRA(pS)AILPG;
```

-continued (SEQ ID NO: 36)
GWTLNSAGYLLGLINLKALAALAKKILSPAARRA(pS)AILPG;

(SEQ ID NO: 37)
PLSSISRIGDPSPAARRA(pS)AILPG;

(SEQ ID NO: 38)
AAVALLPAVLLALLAPSPAARRA(pS)AILPG;

(SEQ ID NO: 39)
AAVLLPVLLAAPSPAARRA(pS)AILPG;

(SEQ ID NO: 40)
VTVLALGALAGVGVGSPAARRA(pS)AILPG;

(SEQ ID NO: 41)
GALFLGWLGAAGSTMGAWSQPSPAARRA(pS)AILPG;

(SEQ ID NO: 42)
GWTLNSAGYLLGLINLKALAALAKKILSPAARRA(pS)AILPG;

(SEQ ID NO: 43)
KLALKLALKALKAALKLASPAARRA(pS)AILPG;

(SEQ ID NO: 44)
KETWWETWWTEWSQPKKKRKVSPAARRA(pS)AILPG;

(SEQ ID NO: 45)
KAFAKLAARLYRKAGCSPAARRA(pS)AILPG;

(SEQ ID NO: 46)
KAFAKLAARLYRAAGCSPAARRA(pS)AILPG;

(SEQ ID NO: 47)
AAFAKLAARLYRKAGCSPAARRA(pS)AILPG;

(SEQ ID NO: 48)
KAFAALAARLYRKAGCSPAARRA(pS)AILPG;

(SEQ ID NO: 49)
KAFAKLAAQLYRKAGCSPAARRA(pS)AILPG, (SEQ ID NO: 50)
AGGGGYGRKKRRQRRRSPAARRA(pS)AILPG;

(SEQ ID NO: 51)
YGRKKRRQRRRSPAARRA(pS)AILPG;

(SEQ ID NO: 1)
YARAAARQARASPAARRA(pS)AILPG;
or (SEQ ID NO: 52)
LTVKSPAARRA(pS)AILPG.

In some embodiments, the polypeptide is selected from (SEQ ID NO: 53)
GRKKRRQRRRPPQARRA(pS)AILPG;

(SEQ ID NO: 54)
AYARAAARQARAARRA(pS)AILPG;

(SEQ ID NO: 55)
DAATATRGRSAASRPTERPRAPARSASRPRRPVEARRA(pS)AILPG;

(SEQ ID NO: 56)
GWTLNSAGYLLGLINLKALAALAKKILARRA(pS)AILPG;

(SEQ ID NO: 57)
PLSSISRIGDPARRA(pS)AILPG;

(SEQ ID NO: 58)
AAVALLPAVLLALLAPARRA(pS)AILPG;

(SEQ ID NO: 59)
AAVLLPVLLAAPARRA(pS)AILPG;

-continued (SEQ ID NO: 60)
VTVLALGALAGVGVGARRA(pS)AILPG;

(SEQ ID NO: 61)
GALFLGWLGAAGSTMGAWSQPARRA(pS)AILPG;

(SEQ ID NO: 62)
GWTLNSAGYLLGLINLKALAALAKKILARRA(pS)AILPG;

(SEQ ID NO: 63)
KLALKLALKALKAALKLAARRA(pS)AILPG;

(SEQ ID NO: 64)
KETWWETWWTEWSQPKKKRKVARRA(pS)AILPG;

(SEQ ID NO: 65)
KAFAKLAARLYRKAGCARRA(pS)AILPG;

(SEQ ID NO: 66)
KAFAKLAARLYRAAGCARRA(pS)AILPG;

(SEQ ID NO: 67)
AAFAKLAARLYRKAGCARRA(pS)AILPG;

(SEQ ID NO: 68)
KAFAALAARLYRKAGCARRA(pS)AILPG;

(SEQ ID NO: 69)
KAFAKLAAQLYRKAGCARRA(pS)AILPG, (SEQ ID NO: 70)
AGGGGYGRKKRRQRRRARRA(pS)AILPG;

(SEQ ID NO: 71)
YGRKKRRQRRRARRA(pS)AILPG;

(SEQ ID NO: 1)
YARAAARQARASPAARRA(pS)AILPG;

(SEQ ID NO: 76)
YARAAARQARAARRA(pS)AILPG;
or (SEQ ID NO: 72)
LTVKARRA(pS)AILPG.

In some embodiments, the polypeptide comprises a sequence that is at least 60% (for example, at least 60%, at least 65%, at least 70%, at least 75%, at least 80%, at least 85%, at least 90%, at least 95%) identical to an amino acid sequence selected from (SEQ ID NO: 53)
GRKKRRQRRRPPQARRA(pS)AILPG;

(SEQ ID NO: 54)
AYARAAARQARAARRA(pS)AILPG;

(SEQ ID NO: 55)
DAATATRGRSAASRPTERPRAPARSASRPRRPVEARRA(pS)AILPG;

(SEQ ID NO: 56)
GWTLNSAGYLLGLINLKALAALAKKILARRA(pS)AILPG;

(SEQ ID NO: 57)
PLSSISRIGDPARRA(pS)AILPG;

(SEQ ID NO: 58)
AAVALLPAVLLALLAPARRA(pS)AILPG;

(SEQ ID NO: 59)
AAVLLPVLLAAPARRA(pS)AILPG;

(SEQ ID NO: 60)
VTVLALGALAGVGVGARRA(pS)AILPG;

-continued

```
                                      (SEQ ID NO: 61)
GALFLGWLGAAGSTMGAWSQPARRA(pS)AILPG;

(SEQ ID NO: 62)
GWTLNSAGYLLGLINLKALAALAKKILARRA(pS)AILPG;

(SEQ ID NO: 63)
KLALKLALKALKAALKLAARRA(pS)AILPG;

(SEQ ID NO: 64)
KETWWETWWTEWSQPKKKRKVARRA(pS)AILPG;

(SEQ ID NO: 65)
KAFAKLAARLYRKAGCARRA(pS)AILPG;

(SEQ ID NO: 66)
KAFAKLAARLYRAAGCARRA(pS)AILPG;

(SEQ ID NO: 67)
AAFAKLAARLYRKAGCARRA(pS)AILPG;

(SEQ ID NO: 68)
KAFAALAARLYRKAGCARRA(pS)AILPG;

(SEQ ID NO: 69)
KAFAKLAAQLYRKAGCARRA(pS)AILPG, (SEQ ID NO: 70)
AGGGGYGRKKRRQRRRARRA(pS)AILPG;

(SEQ ID NO: 71)
YGRKKRRQRRRARRA(pS)AILPG;

(SEQ ID NO: 1)
YARAAARQARASPAARRA(pS)AILPG;

(SEQ ID NO: 76)
YARAAARQARAARRA(pS)AILPG;
or (SEQ ID NO: 72)
LTVKARRA(pS)AILPG.
```

In some aspects, disclosed herein is a polypeptide comprising:
an amino acid sequence according to the general formula X1-X2; wherein
X1 comprises a transduction domain; and
X2 is SPAARRA(pS)AILPG (SEQ ID NO:24); and
wherein pS is phosphoserine.

In some aspects, disclosed herein is a polypeptide comprising:
an amino acid sequence according to the general formula X1-X2; wherein
X1 comprises a transduction domain; and
X2 is ARRA(pS)AILPG (SEQ ID NO:30); and
wherein pS is phosphoserine.

In some embodiments, the one or more polypeptides disclosed herein are phosphorylated.

In some embodiments, Z3 comprises a phosphoserine or a phosphoserine analog. In some embodiments, Z3 comprises a phosphoserine. In some embodiments, Z3 comprises a phosphoserine analog.

According to various embodiments of the polypeptides of the invention, a "pS" residue may be a phosphoserine or a phosphoserine analog (or phosphoserine mimic) Examples of phosphoserine analogs/mimics include, but are not limited to, sulfoserine, amino acid mimics containing a methylene substitution for the phosphate oxygen, 4-phosphono (difluoromethyl)phenylanaline, and L-2-amino-4-(phosphono)-4,4-difuorobutanoic acid. Other phosphoserine mimics can be made by those of skill in the art; for example, see Otaka et al., Tetrahedron Letters 36: 927-930 (1995). In some embodiments, a phosphoserine analog contains a non-hydrolysable linkage to the phosphate group, e.g., a $CF_2$ group. See, e.g., U.S. Pat. No. 6,309,863.

In embodiments where the S residue is phosphorylated, the peptide can be synthesized using a phosphorylated amino acid (or phospho-mimic) during polypeptide synthesis, or the S residue can be phosphorylated after its addition to the polypeptide chain.

In another aspect, the present disclosure provides isolated nucleic acid sequences encoding a polypeptide of the present invention. In further aspects, the present disclosure provides recombinant expression vectors comprising the nucleic acid sequences of the present invention, and host cells transfected with the recombinant expression vectors of the present invention.

In some embodiments, the polypeptides are isolated. In some embodiments, the polypeptides are synthetic. In some embodiments, the polypeptides are recombinant. In some embodiments, the nucleic acid sequences are isolated. In some embodiments, the nucleic acid sequences are synthetic. In some embodiments, the nucleic acid sequences are recombinant.

The transduction of peptide motifs that modulate endothelial function provides for novel peptide-based therapeutics. One of the advantages of this approach is the evolutionary specificity of downstream protein targets. Receptor based modulation of signaling cascades leads to amplifying enzymatic activities. Thus, exploiting specific post-translational modifications of proteomic targets can be more stoichiometric and thus suitable for finer regulation of cellular processes. This approach also has advantages over gene therapy in that there are no delays in protein production or difficulties with regulating the amount of protein expression. Finally, this approach may be feasible for the treatment of specific modalities that are refractory to activation of upstream receptors or signaling cascades. For example, endothelial dysfunction associated with injury occurs coincident with downregulation of the expression of phosphorylated Niban and the polypeptides disclosed herein can recapitulate the endogenous phosphorylated Niban and restore endothelial function.

Compositions

In another aspect, the present disclosure provides pharmaceutical compositions, comprising one or more of the polypeptides disclosed herein, and a pharmaceutically acceptable carrier. Such pharmaceutical compositions are especially useful for carrying out the methods of the invention described below.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol, palmitic acid and octadecanedioic acid. Such linkage can be covalent or non-covalent as is understood by those of skill in the art.

The polypeptides or pharmaceutical compositions thereof may be administered by any suitable route, including orally, parenterally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Embodiments for administration vary with respect to the condition being treated.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

Methods

The polypeptides and compositions disclosed herein comprise non-naturally occurring chimeric polypeptides for use as therapeutic agents for the following: (a) treating or preventing endothelial dysfunction; (b) preventing aging and the consequences of aging (for example, prolonging life (longevity)); (c) treating, preventing and/or reversing atherosclerosis, atherosclerotic lesions, and the consequences of atherosclerosis (myocardial infarction, heart failure, renal failure, stroke, peripheral vascular disease, amputation, death); (d) enhancing techniques for treating atherosclerotic lesions and preventing recurrence (re-stenosis) of atherosclerotic lesions; (e) treating or preventing cardiovascular complications of endothelial dysfunction (angina, myocardial infarction, stroke, death); (f) treating or preventing cardiovascular complications of endothelial dysfunction (angina, myocardial infarction, stroke, death) in patients with metabolic syndrome; (g) treating or preventing arterial stiffness and hypertension and the consequences of arterial stiffness and hypertension (stroke, heart failure); (h) treating or preventing failure of vascular conduits used as bypass grafts; (i) treating or preventing erectile dysfunction; (j) treating or preventing endothelial dysfunction (e.g., acute endothelial dysfunction) associated with injury, burn, acidosis, and/or sepsis and/or (k) to treat or preventing inflammatory diseases (for example, sepsis, rheumatoid arthritis, Crohn's disease, asthma, COPD, chronic pain, cancer).

In some aspects, disclosed herein is a method for restoring endothelial function, comprising: administering to a subject in need thereof an effective amount of a polypeptide disclosed herein.

In some aspects, disclosed herein is a method for restoring endothelial function, comprising: administering to a subject in need thereof an effective amount of a polypeptide comprising:

an amino acid sequence according to the general formula X1-X2; wherein

X1 comprises a transduction domain; and

X2 comprises a polypeptide capable of restoring endothelial function;

wherein X2 includes Z3; and wherein Z3 is selected from a phosphoserine or a phosphoserine analog.

In some aspects, disclosed herein is a method for preventing aging, comprising: administering to a subject in need thereof a therapeutically effective amount of a polypeptide disclosed herein.

In some aspects, disclosed herein is a method for preventing aging, comprising: administering to a subject in need thereof a therapeutically effective amount of a polypeptide comprising:

an amino acid sequence according to the general formula X1-X2; wherein

X1 comprises a transduction domain; and

X2 comprises a polypeptide capable of restoring endothelial function;

wherein X2 includes Z3; and wherein Z3 is selected from a phosphoserine or a phosphoserine analog.

Aging leads to endothelial function and endothelial function contributes to many of the diseases of aging such as coronary artery disease, stroke, hypertension, and diabetes. Thus, preventing or reversing endothelial dysfunction can decrease the morbidity and mortality of these diseases of aging and can increase lifespan.

In some aspects, disclosed herein is a method for restoring endothelial function, comprising: administering to a subject in need thereof an effective amount of a polypeptide comprising: an amino acid sequence according to the general formula X1-X2; wherein X1 comprises a transduction domain; and X2 is SPAARRA(pS)AILPG (SEQ ID NO:24);

wherein pS is phosphoserine.

In some aspects, disclosed herein is a method for treating, preventing and/or reversing atherosclerosis, comprising: administering to a subject in need thereof a therapeutically effective amount of a polypeptide disclosed herein.

In some aspects, disclosed herein is a method for treating atherosclerotic lesions and preventing recurrence (re-stenosis) of atherosclerotic lesions, comprising: administering to a subject in need thereof a therapeutically effective amount of a polypeptide disclosed herein.

In some aspects, disclosed herein is a method for treating or preventing cardiovascular complications of endothelial dysfunction, comprising: administering to a subject in need thereof a therapeutically effective amount of a polypeptide disclosed herein.

In some aspects, disclosed herein is a method for treating or preventing arterial stiffness and/or hypertension, comprising: administering to a subject in need thereof a therapeutically effective amount of a polypeptide disclosed herein.

In some aspects, disclosed herein is a method for treating or preventing failure of vascular conduits used as bypass grafts, comprising: administering to a subject in need thereof a therapeutically effective amount of a polypeptide disclosed herein.

In some aspects, disclosed herein is a method for treating or preventing endothelial dysfunction (e.g., acute endothelial dysfunction) associated with injury, acidosis, burn, or sepsis, comprising: administering to a subject in need thereof a therapeutically effective amount of a polypeptide disclosed herein.

In some aspects, disclosed herein is a method for treating or preventing inflammatory diseases (for example, sepsis, rheumatoid arthritis, Crohn's disease, asthma, COPD), comprising: administering to a subject in need thereof a therapeutically effective amount of a polypeptide disclosed herein.

In some aspects, disclosed herein is a method for treating or preventing chronic pain, comprising: administering to a subject in need thereof a therapeutically effective amount of a polypeptide disclosed herein.

In some aspects, disclosed herein is a method for treating or preventing cancer, comprising: administering to a subject in need thereof a therapeutically effective amount of a polypeptide disclosed herein.

In some embodiments, the inflammatory diseases, chronic pain, and/or cancer are associated with elevated activation levels and/or increased amount of a p38MAPK kinase. The p38MAPK can be, for example, p38α, p38β, p38γ, or p38δ. In some embodiments, the p38MAPK is p38MAPKα.

In another aspect, the disclosure provides methods for the use of a composition comprising a polypeptide comprising an amino acid sequence according to general formula X1-X2; wherein
X1 comprises a transduction domain; and X2 comprises a polypeptide capable of restoring endothelial function; wherein X2 includes Z3; and wherein Z3 is selected from a phosphoserine or a phosphoserine analog, for the preparation of a medicament for carrying out one or more of the following therapeutic uses: (a) treating or preventing endothelial dysfunction; (b) preventing aging and the consequences of aging (for example, prolonging life (longevity)); (c) treating, preventing and/or reversing atherosclerosis, atherosclerotic lesions, and the consequences of atherosclerosis (myocardial infarction, heart failure, renal failure, stroke, peripheral vascular disease, amputation, death); (d) enhancing techniques for treating atherosclerotic lesions and preventing recurrence (re-stenosis) of atherosclerotic lesions; (e) treating or preventing cardiovascular complications of endothelial dysfunction (angina, myocardial infarction, stroke, death); (f) treating or preventing cardiovascular complications of endothelial dysfunction (angina, myocardial infarction, stroke, death) in patients with metabolic syndrome; (g) treating or preventing arterial stiffness and hypertension and the consequences of arterial stiffness and hypertension (stroke, heart failure); (h) treating or preventing failure of vascular conduits used as bypass grafts; (i) treating or preventing erectile dysfunction; (j) treating or preventing endothelial dysfunction (e.g., acute endothelial dysfunction) associated with injury, burn, acidosis, and/or sepsis and/or (k) to treat or preventing inflammatory diseases (sepsis, rheumatoid arthritis, Crohn's disease, asthma, COPD), chronic pain, or cancer.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s). The terms disorder and disease are used interchangeably herein.

As used herein, the term "inhibit" or "inhibiting" means to limit the disorder in individuals at risk of developing the disorder.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

As used herein, "administering" includes in vivo administration, as well as administration directly to tissue ex vivo, such as vein grafts.

In some embodiments of the methods disclosed herein, such as reducing atherosclerotic lesions, the administering may be direct, by contacting a blood vessel in a subject being treated with one or more polypeptides of the invention. For example, a liquid preparation of one or more polypeptides according to the invention can be forced through a porous catheter, or otherwise injected through a catheter to the injured site, or a gel or viscous liquid containing the one or more polypeptides according to the invention can be spread on the injured site. In some embodiments of direct delivery, one or more polypeptides according to the invention can be delivered into cells at the site of injury or intervention. In some embodiments, delivery into cells is accomplished by using the one or more polypeptides according to the invention that include at least one transduction domain to facilitate entry into the cells.

In various other embodiments of the methods disclosed herein, particularly those that involve reducing atherosclerotic lesions, the method is performed on a subject who has undergone, is undergoing, or will undergo a procedure selected from the group consisting of angioplasty, vascular stent placement, endarterectomy, atherectomy, bypass surgery (such as coronary artery bypass surgery; peripheral vascular bypass surgeries), vascular grafting, organ transplant, prosthetic device implanting, microvascular reconstructions, plastic surgical flap construction, and catheter emplacement.

In a further embodiment, the methods disclosed herein are used for treating or preventing endothelial dysfunction. Endothelial dysfunction is associated with aging, diabetes, atherosclerosis, injury, burn, acidosis, and sepsis. Thus, the invention may be used for treating or preventing the complications of diabetes, atherosclerosis, aging, injury, burn, acidosis, and sepsis such as arterial lesions that lead to coronary artery disease, myocardial infarction, heart failure, renal failure stroke, limb loss, vascular hyperpermeability leading to malperfusion/edema, erectile dysfunction, and death.

The polypeptides may be administered systemically or via sustained release systemic administration to treat or prevent endothelial dysfunction or the consequences of endothelial dysfunction and atherosclerosis such as angina, myocardial infarction, stroke, death, limb loss, renal failure, sepsis, or erectile dysfunction. Atherosclerosis is a response to injury over time and is a leading cause of death. Hence, the polypeptides may be administered systemically or via sustained release systemic administration to treat or prevent aging and the consequences of aging resulting in the prolongation of a healthier life (longevity, health span). Prolonged impaired relaxation of blood vessels due to endothelial dysfunction leads to arterial stiffness. Thus, the polypeptides may be used to treat arterial stiffness and the consequences of arterial stiffness such as hypertension, stroke and heart failure.

To treat arterial lesions in coronary, renal, and peripheral artery, bypass grafts composed of prosthetic (dacron, PTFE, etc.) or autogenous (such as saphenous vein) materials may be used. The polypeptides may be used to improve both short and long-term graft success by systemic or local (graft) administration around the time period of graft implantation.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount."

However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

An effective amount of the polypeptides that can be employed ranges generally between about 0.01 µg/kg body weight and about 10 mg/kg body weight (or between about 0.05 µg/kg and about 5 mg/kg body weight). However, dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

As used herein, the term "subject" or "host" can refer to living organisms such as mammals, including, but not limited to humans, livestock, dogs, cats, and other mammals Administration of the therapeutic agents can be carried out at dosages and for periods of time effective for treatment of a subject. In some embodiments, the subject is a mammal. In some embodiments, the subject is a human.

Devices

In another aspect, the disclosure provides improved biomedical devices, wherein the biomedical devices comprise one or more of the polypeptides disclosed herein disposed on or in the biomedical device.

As used herein, a "biomedical device" refers to a device to be implanted into a subject, for example, a human being, in order to bring about a desired result. Example biomedical devices according to this aspect of the invention include, but are not limited to, patches, microneedles, stents, grafts, shunts, stent grafts, fistulas, angioplasty devices, balloon catheters, implantable drug delivery devices, wound dressings such as films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), cellophane, and biological polymers.

As used herein, the term "graft" refers to both natural and prosthetic grafts and implants. In some embodiments, the graft is a vascular graft.

As used herein, the term "stent" includes the stent itself, as well as any sleeve or other component that may be used to facilitate stent placement.

As used herein, "disposed on or in" means that the one or more polypeptides can be either directly or indirectly in contact with an outer surface, an inner surface, or embedded within the biomedical device.

"Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

"Indirect" contact means that the one or more polypeptides do not directly contact the biomedical device. For example, the one or more polypeptides may be disposed in a matrix, such as a gel matrix or a viscous fluid, which is disposed on the biomedical device. Such matrices can be prepared to, for example, modify the binding and release properties of the one or more polypeptides as required.

The present invention may be better understood with reference to the accompanying examples that are intended for purposes of illustration only and should not be construed to limit the scope of the invention, as defined by the claims appended hereto.

EXAMPLES

The following examples are set forth below to illustrate the polypeptides, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Introduction

The inner lining of the vascular wall consists of a monolayer of endothelial cells. Mechanical forces (blood flow disturbances, mechanical stretch), chemical stressors (glycemic, oxidative, osmotic, acidosis), inflammation, and aging are associated with dysfunction of this fragile endothelial monolayer. A common physiologic sequela of endothelial injury is impaired endothelial-dependent relaxation, often referred to as "endothelial dysfunction".

While multiple mechanisms have been implicated in promulgating endothelial injury, one of the common underlying themes is disruption of the endothelial membrane. Measurement of endothelial membrane injury has been performed by measuring extracellular release of biomolecules that have high intracellular concentrations. Adenosine triphosphate (ATP), in which there is a large gradient between intracellular (1-10 mM) and extracellular concentrations (1-10 μM), was one of the first markers of membrane injury. More recently, lactate dehydrogenase (LDH) release has been used as a marker of membrane injury. Loss of endothelial membrane integrity also leads to changes in transcellular resistance which can be measured with impedance (transepithelial/endothelial electrical resistance, TEER). Exposure of veins to acidic saline solutions such as Normal Saline (NS) that is widely used as a resuscitation fluid, or mechanical stretch during surgical harvest leads to endothelial injury and release of ATP, LDH and decreased TEER.

Prolonged exposure to high concentrations of ATP activates the purinergic receptor, P2X7R. P2X7R activation is one of the most potent activators of the inflammasome. P2X7R modulates responses to injury via activation of the p38 mitogen-activated protein kinase (MAPK) signaling pathway. p38 MAPK is also activated by environmental stress and inflammatory cytokines. p38 MAPK modulates a myriad of physiological processes through transcriptional regulation and/or activation of downstream kinases. Thus, increased extracellular ATP after injury is not only a marker of injury, but may also play a role in propagating the vascular "response to injury."

A clinically relevant model of human vascular injury is the process of surgical harvest and preparation of human saphenous vein (HSV) prior to implantation as an autologous transplanted vascular graft. HSV is injured by mechanical stretch during harvest and pressure distention, storage in acidic NS solution, and orientation marking with surgical skin markers. To understand the response to surgical injury, segments of HSV removed atraumatically were compared to cognate segments after to harvest and preparation injury. Injured HSV segments demonstrated impaired endothelial dependent relaxation which was associated with a decrease in Niban phosphorylation. The Niban gene, also known as FAM129A, was first identified as a gene upregulated in cancer. Niban is involved in the regulation of cancer progression, cell proliferation, apoptosis and endoplasmic reticulum (ER) stress responses. Ji et al reported that Akt-dependent phosphorylation of Niban is involved in ultraviolet (UV)-induced cell apoptosis. In Niban knockout mice, the ER stress response pathway was affected as phosphorylation of eukaryotic translational initiation factor (eIF) 2α, p70 ribosomal S6 subunit kinase (S6K) 1, and eukaryotic initiation factor 4E-binding protein (4E-BP) were altered, implicating a role of Niban in modulating translation in cell death signaling. In a rat aorta model of subfailure stretch injury, decreased Niban phosphorylation was associated with an increase in p38 MAPK phosphorylation, supporting the interplay between p38 MAPK after acute vascular injury. Taken together, these data indicate that Niban plays a protective role in response to cellular injury.

In the examples herein, the relationship between p38 MAPK and Niban phosphorylation and the mechanistic interplay of these molecules that contributes to endothelial dysfunction was investigated. Cell-permeant phospho-peptide mimetics of Niban (NiPp) were designed, synthesized, and characterized to function as a therapeutic for treating endothelial dysfunction.

Example 2. Materials and Methods

Materials. All chemicals and reagents were purchased from Sigma unless otherwise described. The peptide (NiPp) used in this study was synthesized by f-moc chemistry and purified using high-performance chromatography by EZBiolab (NJ).

Tissue procurement. Aorta (RA) was procured from 250-300 g, Sprague Dawley rats. Animal procedures followed study protocols approved by the Vanderbilt Institutional Animal Care and Use Committee and adhered to National Institute of Health guidelines for care and use of laboratory animals Immediately after euthanasia by $CO_2$, the thoracic and abdominal RA was isolated via an incision along the mid-abdomen, placed in heparinized PlasmaLyte (PL; 10 unit heparin/mL PlasmaLyte, Baxter, Deerfield IL) and transported to the laboratory for immediate testing.

Human saphenous veins (HSV) was obtained under approval from the Institutional Review Board of Vanderbilt University Medical Center from consented patients undergoing coronary artery bypass grafting procedures. HSV segments were collected immediately following surgical harvest and transported to the laboratory in PL for immediate experimentation.

Measurement of endothelial-dependent relaxation. Rings of HSV or RA (1-2 mm) were suspended in a muscle bath containing a bicarbonate buffer (120 mM sodium chloride, 4.7 mM potassium chloride, 1.0 mM magnesium sulfate, 1.0 mM monosodium phosphate, 10 mM glucose, 1.5 mM calcium chloride, and 25 mM sodium bicarbonate, pH 7.4) equilibrated with 95% $O_2$/5% $CO_2$ at 37° C. for 1 h at a resting tension of 1 g, manually stretched to three times the resting tension, and maintained at resting tension for an additional 1 h.

This produced the maximal force tension relationship as previously described. After equilibration, the rings were primed with 110 mM potassium chloride (with equimolar replacement of sodium chloride in bicarbonate buffer) to determine functional viability. Viable rings were then tested for contractile response to a dose of phenylephrine (PE) to yield submaximal contraction (approximately 60-70% of maximum KCl; $5 \times 10^{-6}$ M for HSV and $1-5 \times 10^{-7}$ M for RA) and relaxed with carbachol (CCH, $5 \times 10^{-7}$ M), an acetylcholine analogue, to determine endothelial-dependent relaxation responses. Force measurements were obtained using the Radnoti force transducer (model 159901A, Radnoti LLC, Monrovia, CA) interfaced with a PowerLab data acquisition system and LabChart software (AD Instruments Inc., Colorado Springs, CO). Contractile responses were defined by stress, calculated using force generated by tissues as follows: stress ($\times 10^5$ N/m$^2$)=force (g)×0.0987/area, where area=wet weight (mg)/at maximal length (mm)]/1.055.

Relaxation was calculated as percent change in stress compared to the maximal PE-induced contraction (set as 100%). Each data point was averaged from at least two rings from the same specimen. To determine concurrent signaling events, tissues were frozen in liquid nitrogen at relevant timepoints.

p38 MAPK activation with Anisomycin. To activate p38 MAPK, thoracic RA were cut into rings and suspended in the muscle bath. Rings were left untreated, treated with anisomycin (200 μM) for 1 h, or pretreated with NiPp (500 μM) for 30 min followed by anisomycin (200 μM) for 1 h.

After treatments, endothelial-dependent relaxation was determined or tissues were snap-frozen for Western blot analysis.

Vascular injury and treatment of RA. Abdominal RA was subjected to subfailure stretch to the haptic endpoint (~200% the resting length) for 10 s and repeated twice as previously described and a segment was reserved as non-stretched control. The tissues were then cut into 1-2 mm rings and incubated for 1 h at room temperature in PL with or without NiPp (500 μM). To induce acidotic injury, thoracic RA were cut into 1-2 mm rings and pretreated in the absence or presence of NiPp (500 μM) in PL for 30 min. Tissue rings were then transferred to NS and continued incubation in the absence or presence of NiPp (500 μM) for 2 h. Control rings were incubated in PL for 2.5 h.

To induce P2X7R associated endothelial dysfunction, thoracic RA rings were incubated with the P2X7R agonist 2'(3')-O-(4-Benzoylbenzoyl)adenosine 5'-triphosphate (BzATP; 1 mM) in the absence or presence of NiPp (500 μM) in PL for 1 h at room temperature. After treatments, RA were either suspended in the muscle bath to determine endothelial-dependent relaxation or snap-frozen for Western blot analysis.

Western blot Analysis. Frozen tissues were pulverized, and proteins were extracted in modified RIPA buffer (50 mM Tris-Cl, 150 mM NaCl, 1% NP40, 0.5% deoxycholic acid, 1 mM EDTA, 1 mM EDTA) supplement with protease and phosphatase inhibitors. Protein were subjected to SDS-PAGE and transferred to a nitrocellulose membrane followed by immunoblotting with the antibodies against phospho-p38 MAPK-Thr180/Tyr182, p38 MAPK, (Cell Signaling Technology, CA), and GAPDH (Millipore, MA). The blots were then incubated with IRDye labeled secondary antibodies (LI-COR Biosciences, NE). The protein-antibody complexes were visualized and quantified using the Odyssey Infrared Imaging System. Phosphorylation was calculated as a ratio of the phosphorylated protein to total protein and was then normalized to the untreated tissues (Ctrl) with the control value set as 1.0.

Kinase profiling. NiPp was dissolved in DMSO, screened at a single concentration of 100 μM using in vitro kinase assays (SelectScreen Kinase Profiling Service; ThermoFisher Scientific, Madison WI) including the Z'LYTE and Adapta kinase activity assays and the LanthaScreen Eu Kinase Binding Assay). Candidate interactions were predicted using STRING Version 11 (www.string-db-org) with the human database at confidence=0.7.

Peptide Synthesis and Purification. Peptides were synthesized using standard f-moc chemistry and purified using high performance liquid chromatography (HPLC) by EZ Biolabs (Carmel, IN).

Muscle bath studies. Tissue rings were suspended in bicarbonate buffer in the muscle bath at 37° C., equilibrated with 95% O2/5% CO2 at 37° C. for 1 hour. Rings were manually stretched to 3 grams of tension, followed by a resting tension of 1 gram for an additional 1 hour to produce a maximal force-tension relationship. Next, rings were contracted with 110 mM potassium chloride to determine functional viability. The tissues were then precontracted with phenylephrine and relaxed with carbachol, an acetylcholine analogue. Force measurements were obtained using the Radnoti force transducer (model 159901A, Radnoti LLC, Monrovia, CA) interfaced with a PowerLab data acquisition system and LabChart software (AD Instruments Inc., Colorado Springs, CO). Relaxation was calculated as percent change in stress compared to the maximal PE-induced contraction (set as 100%).

Statistical Analysis. Data were reported as mean responses±standard deviation. Outliers, normality, and statistical significance (p value) were determined using GraphPad Prism version 5.0. Differences among groups were determined by paired t test for experiments with dependent (matched) pairs. One-way or two-way ANOVA with post hoc tests were used to determine differences among multiple, dependent samples from the same animal A $p$-value$<0.05$ was considered statistically significant.

Example 3. Aging Leads to Decreased Endothelial Function in Rodent Blood Vessels This example illustrates that aging leads to decreased endothelial function in rodent blood vessels. Freshly isolated aorta from young (4 months) and old (20 months) rats were suspended in the muscle bath. To determine the effect of injury on endothelial function, phenylephrine (PE)-precontracted tissues were treated with carbachol (CCH; $5\times10^{-7}$ M) and the percent relaxation was determined as a change to the maximal PE-induced contraction. The result of this experiments is illustrated in FIG. 1. This study shows that old rats have decreased endothelial function.

Figure 2:
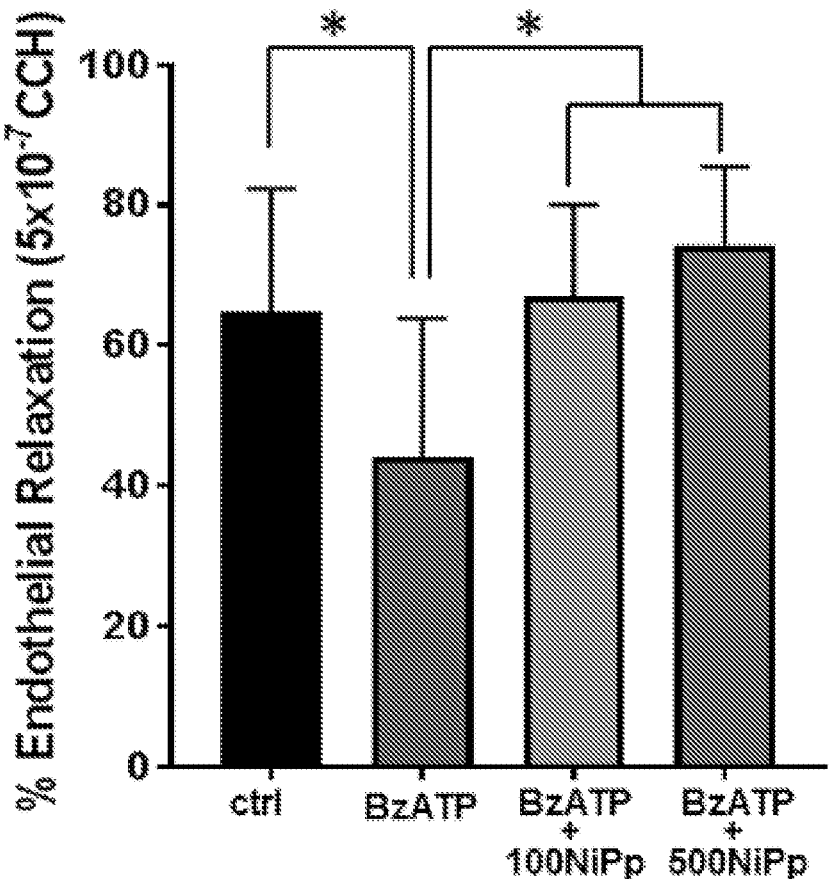
FIG. 2 shows that the NiPp polypeptide (SEQ ID NO:1) restores endothelial function in rodent aortic tissue after ATP injury. Freshly isolated rat aorta was treated with 3'-O-(4-Benzoyl)benzoyl adenosine 5'-triphosphate (BzATP, 1 mM), an analogue of ATP, to induce injury in the absence or presence of NiPp (100 and 500 μM) for 1 hour at room temperature. To determine the effect of injury on endothelial function, phenylephrine (PE)-precontracted tissues were treated with carbachol (CCH; $5\times10^{-7}$ M) and the percent relaxation was determined as a change to the maximal PE-induced contraction. Data are reported as mean responses±standard deviation. n=5-6. *p<0.05, paired t-test.
Figure 11A:
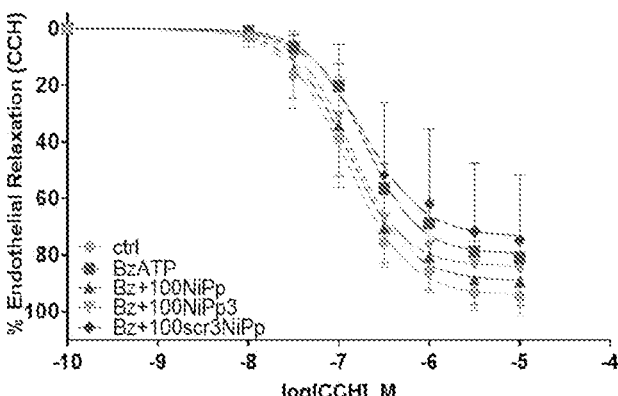
FIGS. 11A and 11B show that NiPp3 (non-P) or scr3NiPp (scrambled) did not restore BzATP-induced endothelial dysfunction in rat aorta. Freshly isolated rat aorta was treated with 3'-O-(4-Benzoyl)benzoyl adenosine 5'-triphosphate (BzATP, 1 mM), an analogue of ATP, to induce injury in the absence or presence of NiPp, NiPp3, or scr3NiPp (A, 100 and B, 500 μM) for 1 hour at room temperature. To determine the effect of injury on endothelial function, phenylephrine (PE)-precontracted tissues were treated with escalating doses of carbachol (CCH; $10^{-10}$ to $10^{-5}$M) and the percent relaxation was determined as a change to the maximal PE-induced contraction. n=7. *p<0.05, two-way ANOVA with Tukey post-tests. There were significant differences between BzATP-treated vs ctrl or NiPp-treated RA. NiPp3 (non-P) and scr3NiPp (scrambled) did not restore BzATP-induced endothelial dysfunction in RA indicating the specificity of NiPp activity.
Figure 11B:
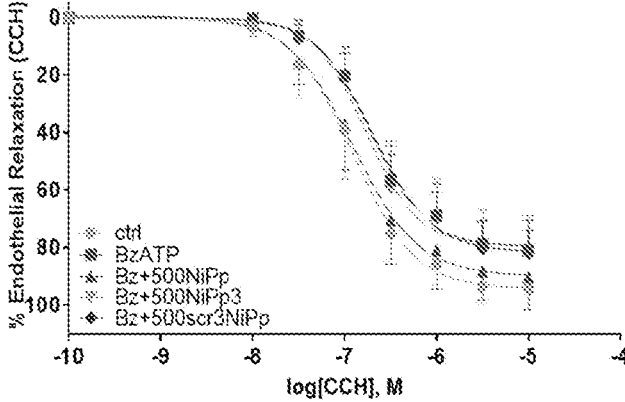

Example 4. Restoring Endothelial Function in Rodent Aortic Tissue after ATP Injury This experiment demonstrates that the NiPp polypeptide [YARAAARQARASPAARRA(pS)AILPG (SEQ ID NO:1); where X1=YARAAARQARA (SEQ ID NO:22) and X2=SPAARRA(pS)AILPG (SEQ ID NO:24)] restores endothelial function in rodent aortic tissue after ATP injury. Freshly isolated rat aorta was treated with 3'-O-(4-Benzoyl) benzoyl adenosine 5'-triphosphate (BzATP, 1 mM), an analogue of ATP, to induce injury in the absence or presence of NiPp (100 and 500 μM) for 1 hour at room temperature. To determine the effect of injury on endothelial function, phenylephrine (PE)-precontracted tissues were treated with carbachol (CCH; $5\times10^{-7}$M) and the percent relaxation was determined as a change to the maximal PE-induced contraction. The result of the experiment is illustrated in FIG. 2. The experiment demonstrates that ATP injury leads to decreased endothelial function that is restored by treatment with NiPp. As control sequences, the portion of the NiPp polypeptide corresponding to the X2 Nib an polypeptide was scrambled or containing non-phosphorylated Serine and used as controls (scr3NiPp=SEQID No. 79, [YARAAARQARAAPA (pS)ARIALPGSR (SEQ ID NO:2); where X1=YARAAARQARA (SEQ ID NO:22) and X2=APA(pS) ARIALPGSR (SEQ ID NO:73) and NiPp3=SEQ ID NO:77]. The result of the experiment is illustrated in FIGS. 11A and B.

Figure 3:
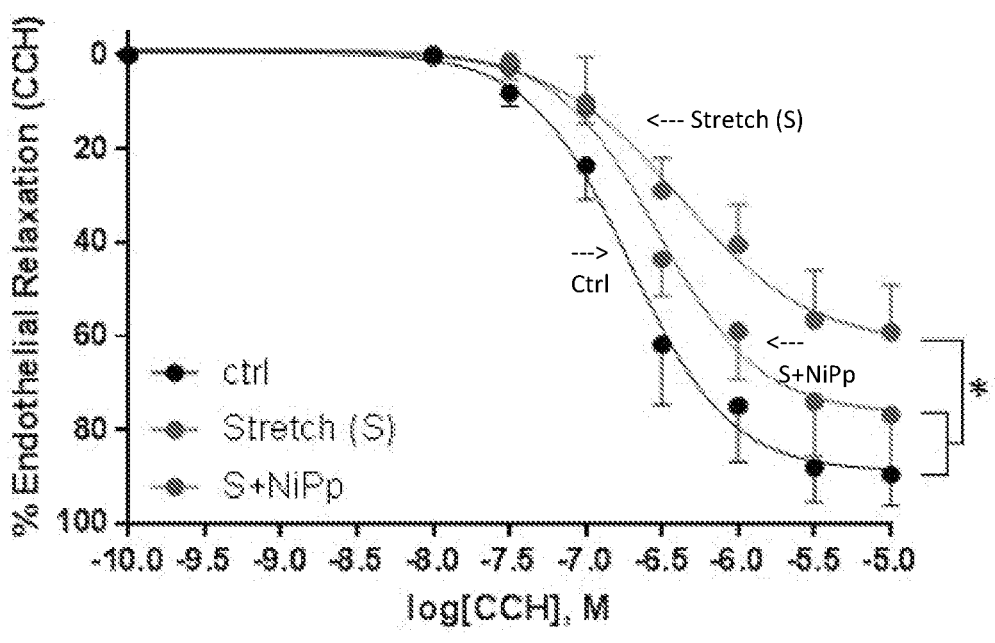
FIG. 3 shows that the NiPp polypeptide (SEQ ID NO:1) restores endothelial function in rodent aortic tissue after stretch (mechanical) injury. Freshly isolated rat aorta was subjected to subfailure stretch (to haptic endpoint, approximately 2 times the resting length and treated with NiPp (500 μM) for 1 hour at room temperature. To determine the effect of injury on endothelial function, phenylephrine-precontracted tissues were treated with carbachol (CCH; $10^{-8}$ to $10^{-5}$M) and the percent relaxation was determined as a change to the maximal PE-induced contraction. Data are reported as mean responses±standard deviation. n=5. *p<0.05, two-way ANOVA.
Figure 13:
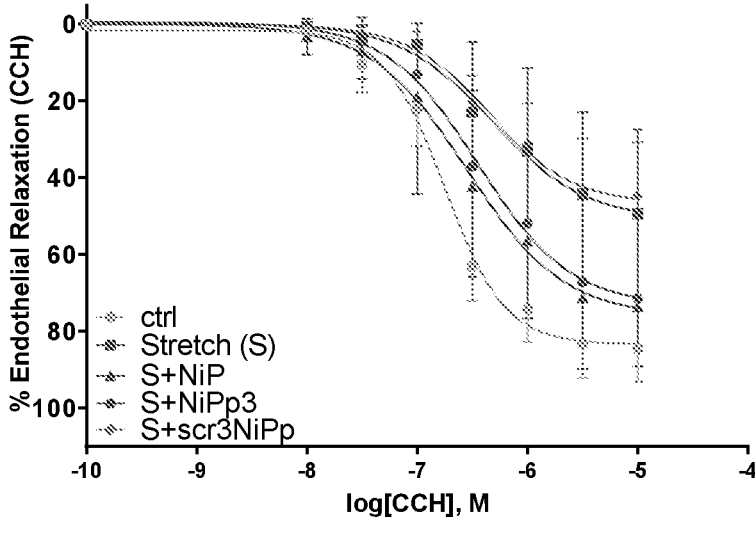
FIG. 13 shows that NiPp3 (non-P) or scr3NiPp (scrambled) did not restore stretch-induced endothelial dysfunction in rat aorta. Freshly isolated rat aorta was subjected to subfailure stretch (to haptic endpoint, approximately 2 times the resting length) and treated with NiPp, NiPp3, or scr3NiPp (500 μM) for 1 hour at room temperature. To determine the effect of injury on endothelial function, phenylephrine-precontracted tissues were treated with carbachol (CCH; $10^{-8}$ to $10^{-5}$M) and the percent relaxation was determined as a change to the maximal PE-induced contraction. Data are reported as mean responses±standard deviation. n=8. *p<0.05, two-way ANOVA with Tukey post-tests. There were significant differences between Stretch (S) vs. ctrl or NiPp-treated RA. NiPp3 (non-P) and scr3NiPp (scrambled) did not restore stretch-induced endothelial dysfunction in RA indicating the specificity of NiPp activity.
Figures 14A, 14B:
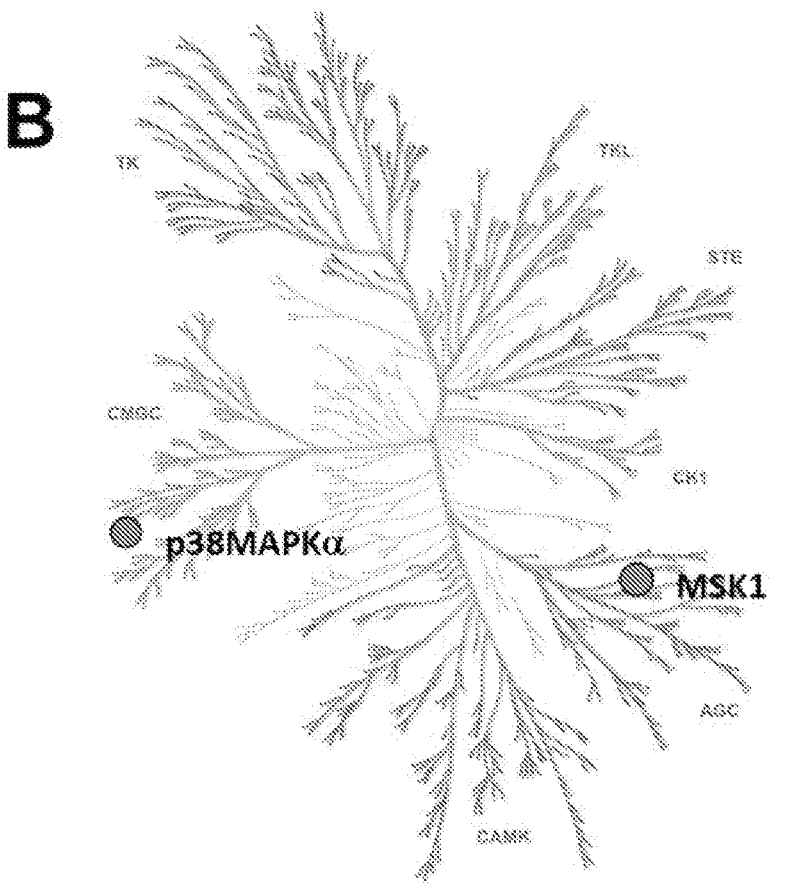
FIGS. 14A and 14B show kinase profiling of polypeptides. NiPp, scr3NiPp, and NiPp3 were profiled against 490 kinases at 100 uM using the SelectScreen Kinase Profiling Service (www.thermofisher.com).
Figures 15A, 15B, 15C, 15D:
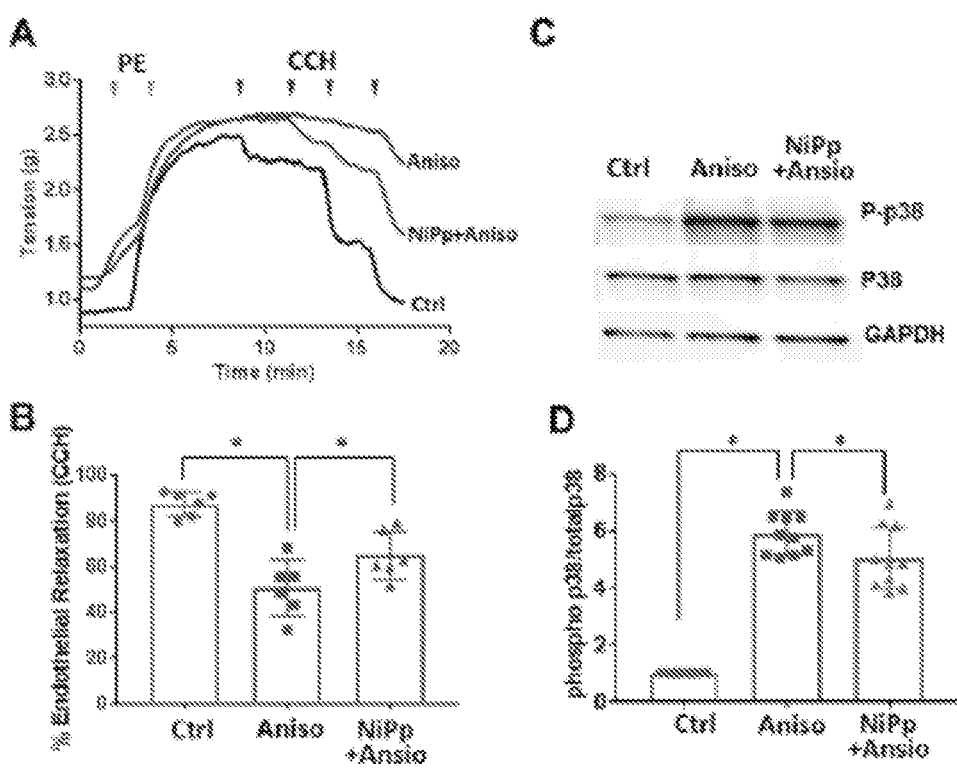
FIGS. 15A to 15D show that anisomycin-induced phosphorylation of p38 MAPK and decreased carbachol (CCH)-induced relaxation in rat aorta (RA) is prevented by treatment with Niban peptide (NiPp). RA rings were suspended in a muscle bath and incubated with either buffer alone (Ctrl), Aniso (200 μM) for 1 h, or NiPp (500 μM) for 30 min followed by Aniso (200 μM) for 1 h.

Example 5. Restoring Endothelial Function in Rodent Aortic Tissue after Stretch (Mechanical) Injury This study shows that the NiPp polypeptide (SEQ ID NO:1) restores endothelial function in rodent aortic tissue after stretch (mechanical) injury. Freshly isolated rat aorta was subjected to subfailure stretch (to haptic endpoint, approximately 2 times the resting length) and treated with NiPp (500 μM) for 1 hour at room temperature. To determine the effect of injury on endothelial function, phenylephrine-precontracted tissues were treated with carbachol (CCH; $10^{-8}$ to $10^{-5}$M) and the percent relaxation was determined as a change to the maximal PE-induced contraction. The result of the experiments is illustrated in FIG. 3. The result of this study demonstrates that stretch injury leads to decreased endothelial function that is restored by treatment with NiPp. Control peptides (SEQ ID NOs:77 and 79) did not restore BzATP-induced endothelial dysfunction in RA indicating the specificity of NiPp activity. The result of the experiment is illustrated in FIG. 13.

Figure 4:
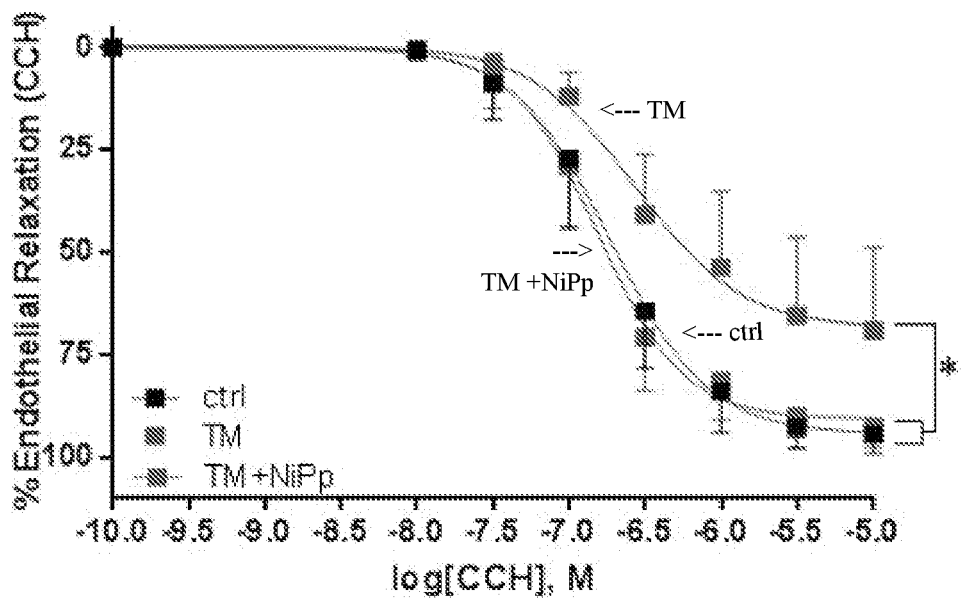
FIG. 4 shows that the NiPp polypeptide (SEQ ID NO:1) restores endothelial function in rodent aortic tissue after endoplasmic reticulum stress (tunicamycin) injury. Freshly isolated rat aorta was treated with tunicamycin (TM) to induce injury in the absence or presence of NiPp (100 and 500 μM) for 2 hours at room temperature. To determine the effect of injury on endothelial function, phenylephrine (PE)-precontracted tissues were treated with carbachol (CCH; $10^{-8}$ to $10^{-5}$M) and the percent relaxation was determined as a change to the maximal PE-induced contraction. Data are reported as mean responses±standard deviation. n=6. *p<0.05, two-way ANOVA.

Example 6. Restoring Endothelial Function in Rodent Aortic Tissue after Endoplasmic Reticulum Stress (Tunicamycin) Injury This experiment shows that the NiPp polypeptide (SEQ ID NO:1) restores endothelial function in rodent aortic tissue after endoplasmic reticulum stress (tunicamycin) injury. Freshly isolated rat aorta was treated with tunicamycin (TM) to induce injury in the absence or presence of NiPp (100 and 500 $\mu$M) for 2 hours at room temperature. To determine the effect of injury on endothelial function, phenylephrine (PE)-precontracted tissues were treated with carbachol (CCH; $10^{-8}$ to $10^{-5}$M) and the percent relaxation was determined as a change to the maximal PE-induced contraction. The result of the experiments is illustrated in FIG. 4. The experiment shows that injury leads to decreased endothelial function that is restored by treatment with NiPp.

Example 7. Restoring Endothelial Function in Aged Human Saphenous Veins (HSV)

Figure 5:
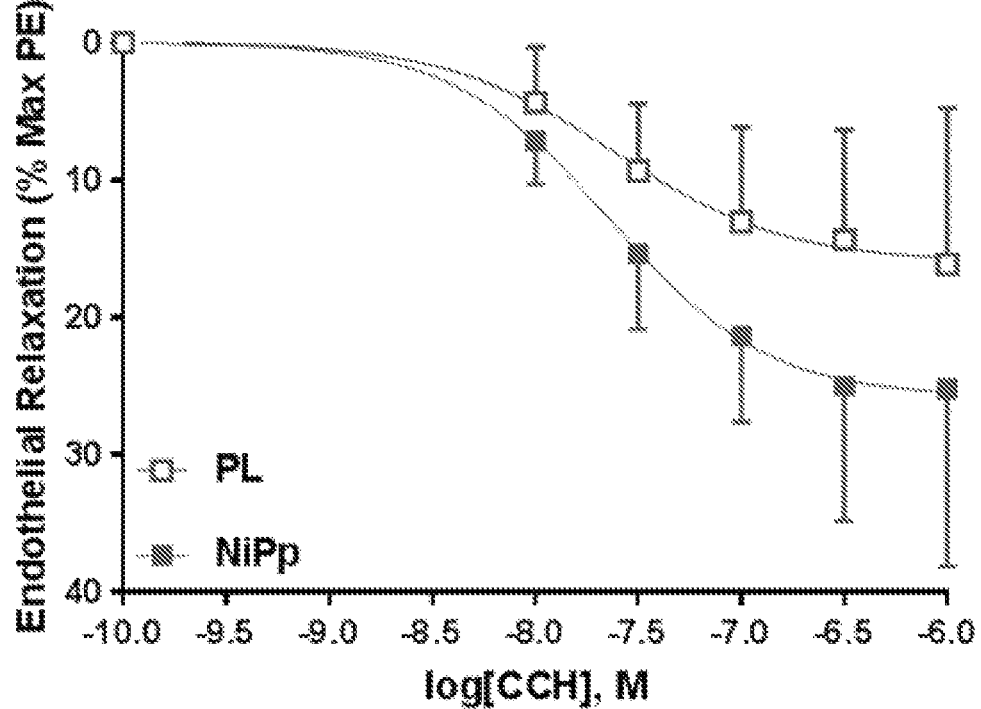
FIG. 5 shows that the NiPp polypeptide (SEQ ID NO:1) restores endothelial function in aged human saphenous veins. Human saphenous veins (HSV) were collected from patients undergoing coronary artery bypass grafting procedures and treated with NiPp (500 μM) for 1 hour at room temperature. PE-precontracted tissues were treated with carbachol (CCH; $10^{-8}$ to $10^{-5}$M). Percent relaxation was determined as a change to the maximal PE-induced contraction. Data are reported as mean responses±standard deviation. n=2. Baseline endothelial function in HSV was low. Treatment with NiPp led to increased endothelial function in human saphenous veins (HSV).
Figure 7A:
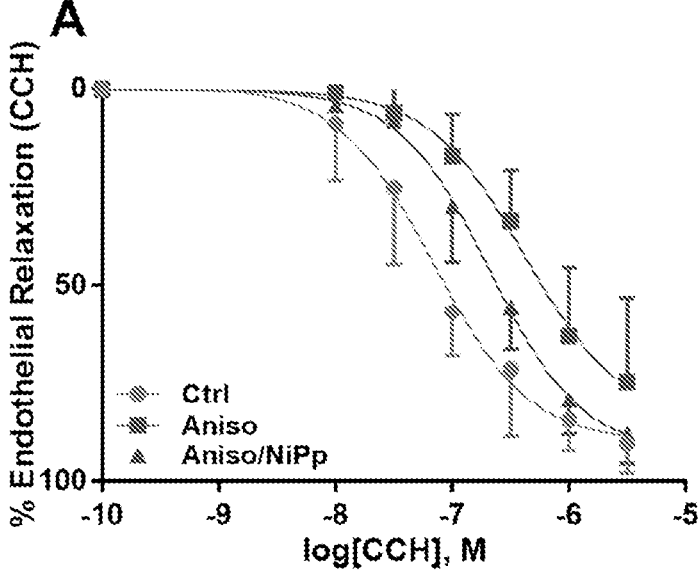
FIGS. 7A and 7B show that anisomycin-induced phosphorylation of p38 MAPK and decreased carbachol (CCH)-induced relaxation in rat aorta (RA) is prevented by treatment with Niban peptide (NiPp). RA rings were suspended in a muscle bath and incubated with either buffer alone (Ctrl), Aniso (200 μM) for 1 h, or NiPp (500 μM) for 30 min followed by Aniso (200 μM) for 1 h.
Figure 7B:
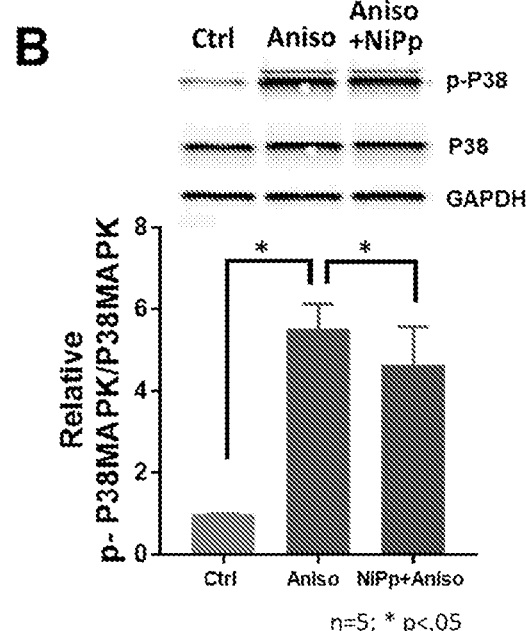

This study illustrates that the NiPp polypeptide (SEQ ID NO:1) restores endothelial function in aged human saphenous veins. Human saphenous veins (HSV) were collected from patients undergoing coronary artery bypass grafting procedures and treated with NiPp (500 $\mu$M) for 1 hour at room temperature. PE-precontracted tissues were treated with carbachol (CCH; $10^{-8}$ to $10^{-5}$M). The result of the experiments is illustrated in FIG. 5. The result of this study shows that baseline endothelial function in human saphenous veins (HSV) is low. The result of this study also demonstrates that treatment with NiPp leads to increased endothelial function in HSV. When normalized to baseline relaxation, NiPp leads to 183±24% in relaxation responses in HSV.

Example 8. Design of Phosphomimetic of Niban, NiPp

Phosphorylation of Niban at serine 602 is downregulated during UV-induced cell death and injured vascular tissues. A peptide (Niban phosphopeptide, "NiPp") was designed to contain the enhanced protein transduction domain TAT, conjugated to a phosphopeptide analog of the region surrounding serine 602 of Niban (YARAAARQARASPAAR-RA(pS)AILPG (SEQ ID NO:1); bold=Niban sequence). Multiple batches were synthesized and displayed similar bioactivity (FIG. 18).

Example 9. Anisomycin Treatment Activates p38 MAPK and Impairs Endothelial Function of Intact Rat Aortic Tissues Intact strips of rat aorta (RA) were treated with anisomycin, an antibiotic produced by *Streptomyces griseolus* known to induce p38 MAPK activation in endothelial cells. Anisomycin treatment led to increases in the phosphorylation of p38 MAPK and impaired endothelial dependent relaxation (FIGS. 15A to 15D).

Example 10. NiPp Reduced p38 MAPK Phosphorylation and Restored Endothelial Function in Anisomycin-Treated Rat Aorta Using the model of impaired endothelial-dependent relaxation in anisomycin treated vessels, RA was treated with buffer alone, anisomycin or NiPp for 30 minutes followed by anisomycin. Pre-treatment with NiPp improved endothelial-dependent relaxation and decreased anisomycin-induced increases in p38 MAPK phosphorylation (FIGS. 15A to 15D).

Figures 8A, 8B:
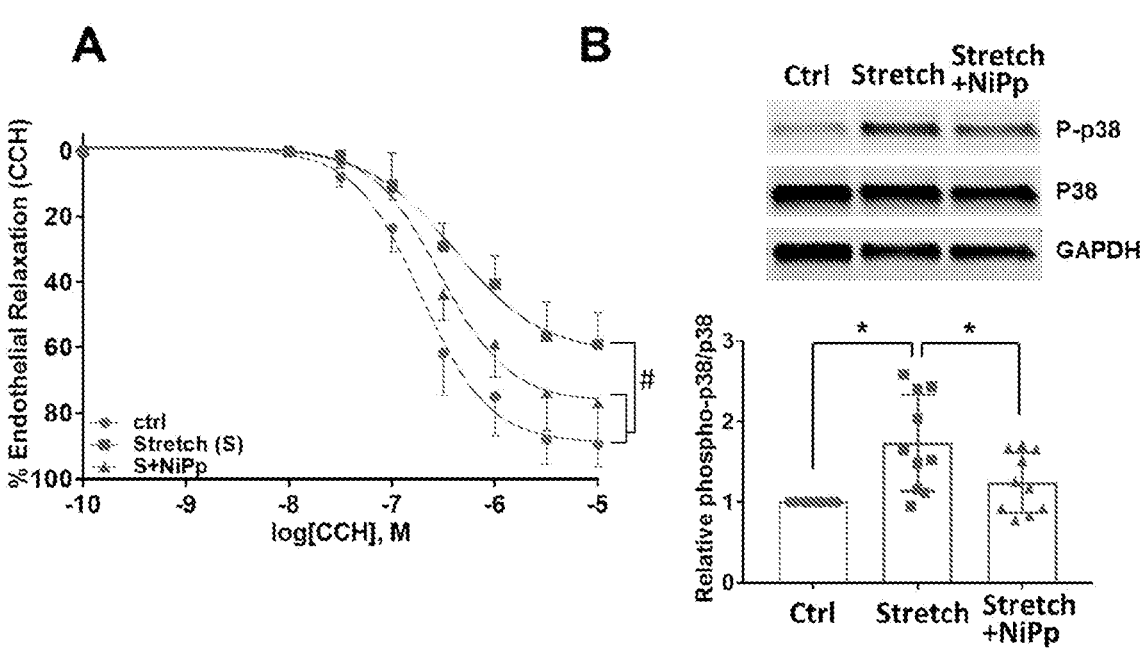
FIGS. 8A and 8B show that NiPp restores endothelial function and reduces p38MAPK phosphorylation in rodent aortic tissue after subfailure stretch injury. Freshly isolated rat aorta (RA) was subjected to subfailure stretch and incubated in PL in the absence (S) or presence of NiPp (500 μM) for 1 h at room temperature.
Figure 9:
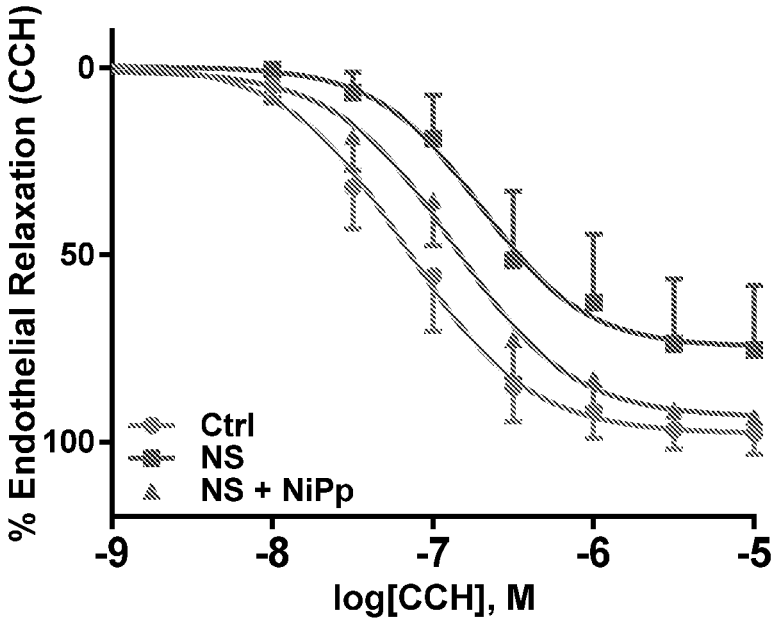
FIG. 9 shows that NiPp restores endothelial function in rodent aortic tissues after acidosis injury. Freshly isolated rat aorta (RA) was cut into rings and then pretreated in the absence or presence of NiPp (500 μM) in PL for 30 min. Tissue rings were then transferred to normal saline (NS) to induce injury in the absence or presence of NiPp (500 μM) and continued incubation for 2 h at room temperature. After treatments, RA were suspended in the muscle bath, contracted with PE and then treated with escalating doses of carbachol (CCH; $10^{-8}$ to $10^{-5}$ M). The percent relaxation was determined as a change to the maximal PE-induced contraction. n=5-7 rats. *p<0.05 in two-way ANOVA with Tukey post-test. NiPp restores NS-induced endothelial dysfunction in RA.

Example 11. NiPp Restored Endothelial Function and Reduced p38 MAPK Phosphorylation after Subfailure Stretch Injury in Rat Aorta To determine if NiPp restores endothelial function after other types of injury, RA was subjected to stretch injury and treated with NiPp. NiPp restored endothelial function after stretch injury (FIG. 8A) and reduced p38 MAPK phosphorylation (FIGS. 8B and 8C).

Figures 16A, 16B:
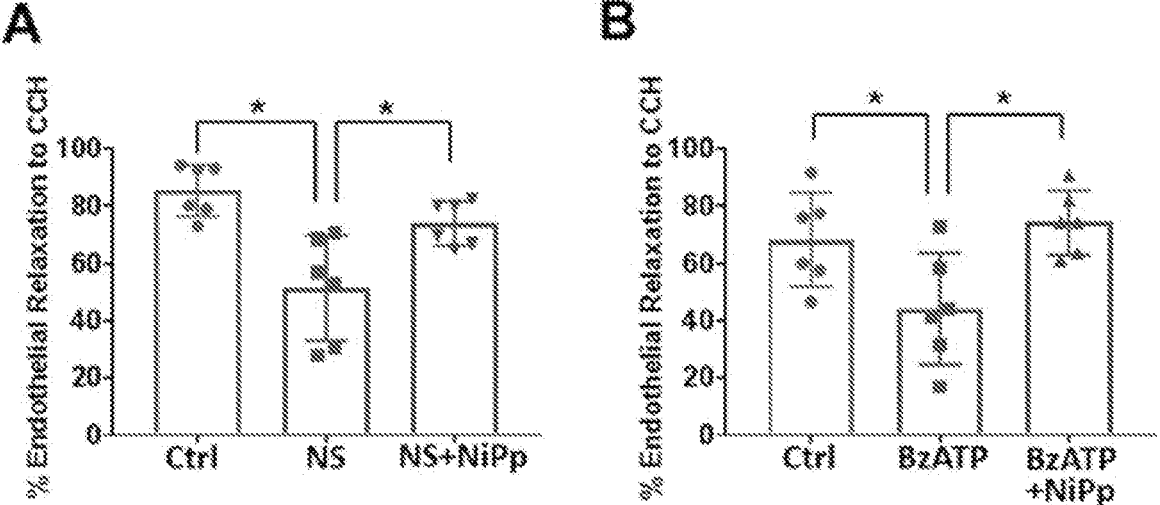
FIGS. 16A and 16B show that NiPp restores endothelial function in rodent aortic tissues after acidosis injury and P2X7R activation.

Example 12. NiPp Restored Endothelial Function after Acidosis Injury and P2X7R Activation in Rat Aorta An additional, clinically relevant type of injury is exposure to acidic NS solution commonly used clinically for intravenous resuscitation and for storage of vascular tissues prior to use as autologous vascular reconstruction conduits. Pre-treatment with NiPp improved endothelial function in RA incubated in NS (FIG. 16A).

Both stretch and NS induced injury lead to release of ATP and activation of P2X7R. RA were treated with the ATP analogue, BzATP, a potent and specific P2X7R agonist in the presence of NiPp. NiPp co-treatment prevented endothelial dysfunction induced by BzATP (FIG. 16B)

Figure 10:
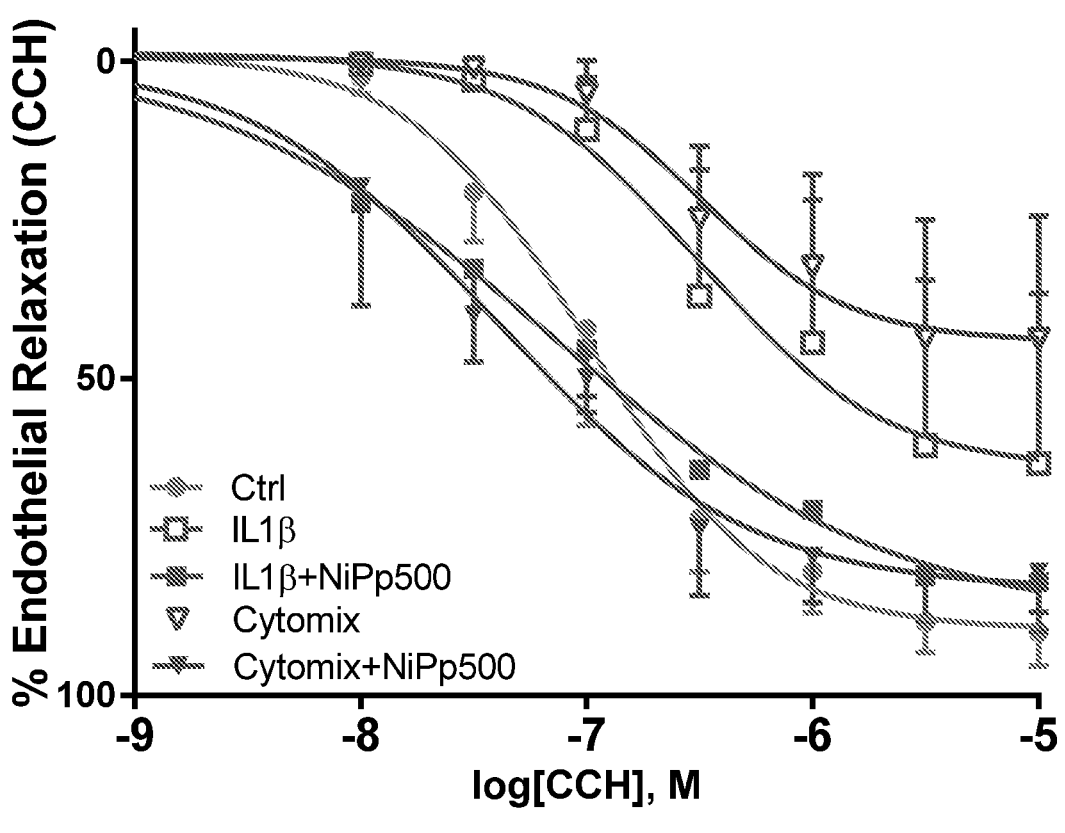
FIG. 10 shows that NiPp restores endothelial function in rodent aortic tissues after cytokines injury. Freshly isolated rat aorta (RA) was cut into rings and suspended in the muscle bath. Tissues were then treated with either IL1β alone (50 ng/ml) or cytomix (IL1β 50 ng/ml, TNFa, 10 ng/ml, IFNg 50 ng/ml) in the absence or presence of NiPp (500 μM) for 2 hrs, contracted with PE, and then treated with escalating doses of carbachol (CCH; $10^{-8}$ to $10^{-5}$M). The percent relaxation was determined as a change to the maximal PE-induced contraction. n=5-7 rats. *p<0.05 in two-way ANOVA with Tukey post-test. NiPp restores cytokines-induced endothelial dysfunction in RA.

Example 13. NiPp Improved Endothelial Function after Cytokine Injury in Rat Aorta Freshly isolated rat aorta (RA) was cut into rings and suspended in the muscle bath. Tissues were then treated with either IL1$\beta$ alone (50 ng/ml) or cytomix (IL1$\beta$ 50 ng/ml, TNFa, 10 ng/ml, IFNg 50 ng/ml) in the absence or presence of NiPp (500 $\mu$M) for 2 hrs, contracted with PE, and then treated with escalating doses of carbachol (CCH; 10–8 to 10–5 M). The NiPp3 treatment group exhibited significant improvement of endothelial relaxation in comparison to IL1$\beta$ or cytomix treatment group, indicating that NiPp improved endothelial function after cytokine injury (FIG. 10).

Figure 12:
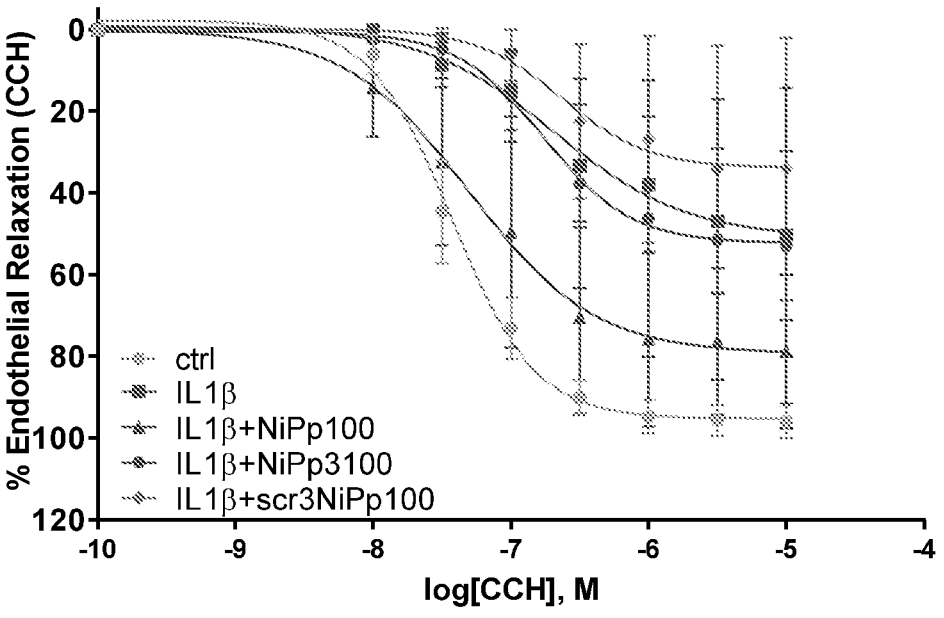
FIG. 12 shows that NiPp restores endothelial function in rodent aortic tissues after cytokine injury. Freshly isolated rat aorta (RA) was cut into rings and suspended in the muscle bath. Tissues were then treated with the cytokine IL1β (50 ng/ml) in the absence or presence of NiPp, NiPp3, or scr3NiPp (100 μM) for 2 hrs, contracted with PE, and then treated with escalating doses of carbachol (CCH; $10^{-8}$ to $10^{-5}$ M). The percent relaxation was determined as a change to the maximal PE-induced contraction. n=5-7 rats. *p<0.05 in two-way ANOVA with Tukey post-tests. There were significant differences between IL1β-treated vs ctrl or NiPp-treated RA. NiPp3 (non-P) and scr3NiPp (scrambled) did not restore IL1β-induced endothelial dysfunction in RA indicating the specificity of NiPp activity.

Freshly isolated rat aorta (RA) was cut into rings and suspended in the muscle bath. Tissues were then treated with the cytokine IL1$\beta$ (50 ng/ml) in the absence or presence of NiPp, NiPp3, or scr3NiPp (100 $\mu$M) for 2 hrs, contracted with PE, and then treated with escalating doses of carbachol (CCH; $10^{-8}$ to $10^{-5}$ M). NiPp3 (SEQ ID NO:77) is a control polypeptide containing non-phosphorylated sequence of X2 of NiPp. scr3NiPp3 (SEQ ID NO:79) is a control polypeptide containing scrambled sequence of X2 of NiPp. The NiPp3 treatment group exhibited significant improvement of endothelial relaxation, whereas scr3NiPp3 and NiPp3 failed to restore endothelial function (FIG. 12).

Example 14. NiPp Improved Endothelial Function
in Human Saphenous Vein Harvested for Coronary
Artery Bypass Surgery To determine the effect of NiPp on human tissues with
endogenous impaired endothelial function, segments of
HSV were harvested at the time of coronary artery bypass
surgery. The tissues were either untreated or incubated in the
presence of NiPp for 2 hours and endothelial responses were
determined. Treatment with NiPp improved endothelial-
dependent relaxation (FIGS. 17A and 17B).

Example 15. NiPp is a Kinase Inhibitor

As injury leads to increased p38 MAPK phosphorylation
and decreased Niban phosphorylation, one of the mecha-
nisms by which NiPp restores function after endothelial
injury can be kinase inhibition. A kinase profiling was
performed using three different profiling platforms that
measure activity and kinase/substrate binding. Kinases of
which activity or substrate binding were inhibited by NiPp
(100 μM) at >40% are listed and shown in a kinase den-
drogram (FIGS. 14A, 14B, 19A and 19B).

Figures 19A, 19B, 19C:
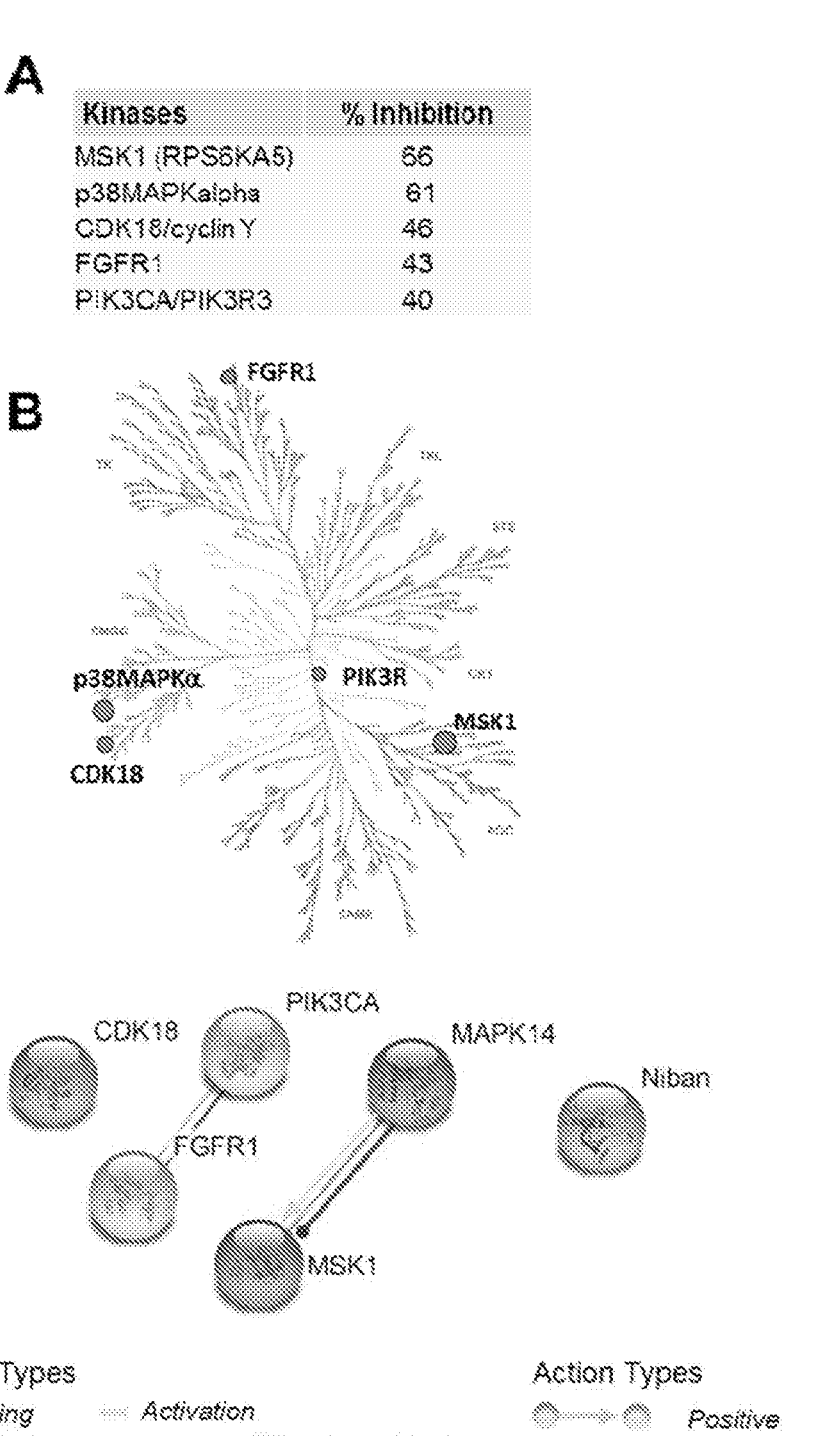
FIGS. 19A to 19C show kinase profiling of NiPp.

The top two candidate kinase targets of NiPp were mito-
gen- and stress-activated kinase 1 (MSK1; also known as
RPS6KA5) and p38 MAPKα (MAPK14), which were inhib-
ited by 66% and 61%, respectively. MSK1 is an AGC kinase
of the RSK family that is phosphorylated by ERK and p38
MAPK in response to cellular stress. Other kinases inhibited
by the NiPp include CKD18 of the CMGC kinase family),
FGFR1 of the TK family, and the PIK3R3 kinase (FIGS.
19A and 19B).

Example 16. Discussion p38 MAPK activation after vascular injury is associated
with endothelial dysfunction and decreased Niban phospho-
rylation, indicating a link between the two proteins. This
study demonstrated that pharmacological activation of p38
MAPK with anisomycin was modulated by NiPp, a phos-
phopeptide mimetic of Niban. NiPp pre-treatment reduced
p38 MAPK phosphorylation and prevented endothelial dys-
function, implicating that NiPp can ameliorate injury
responses that involve p38 MAPK signaling. p38 MAPK is
activated in response to multiple cellular stressors including
infection, UV exposure, and ischemic injury of the brain,
kidney, liver, and heart. p38 MAPK also responds to inflam-
matory cytokines and is a key mediator of inflammatory
responses. In the vascular wall, p38 MAPK is activated
following balloon or bypass grafting related injuries and
promotes neointima formation. Niban is characterized as an
ER stress-related, anti-apoptotic protein. A number of stud-
ies demonstrate that ER stress plays a role in endothelial
dysfunction and leads to p38 MAPK activation. Acidosis,
P2X7R activation, and mechanical stretch are also known to
induce ER stress signaling in various cell types. The present
investigation further shows that impaired endothelial
responses caused by with these injuries in RA, all of which
lead to increases in p38 MAPK phosphorylation, were
restored with NiPp treatment. Impaired endothelial function
is associated with aging, atherosclerosis, diabetes and renal
failure. Saphenous vein harvested for coronary reconstruc-
tions were obtained from an aged patient population
(66.4±8.8 yrs old) with systemic atherosclerosis and mul-
tiple co-morbidities (FIGS. 17A and 17B). Human saphen-
ous veins (HSV) obtained from this population displays
impaired endothelial dependent relaxation (10-15% at 5×10⁻

Figure 20:
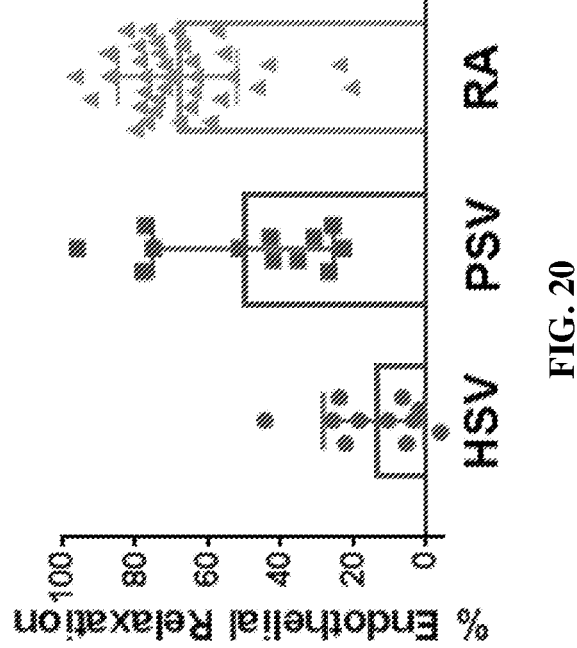
FIG. 20 shows comparison of endothelial-dependent relaxation of vascular tissues from different species. Data from previous studies on endothelial function of saphenous veins collected from patients undergoing coronary artery bypass procedures or healthy adult pigs, and thoracic aorta collected from healthy adult rats were plotted for comparison. Basal endothelial-dependent relaxation was determined in the muscle bath by precontracting with sub-maximal doses of phenylephrine and relaxed with $5\times10^{-7}$M CCH.

7M CCH) compared to normal healthy tissues from young
animals such as pigs or rats (~50-70%; FIG. 20). Thus, HSV
represents a model of endogenous endothelial dysfunction in
human tissue.

Treatment of HSV with NiPp resulted in improvement of
endothelial-dependent relaxation (FIGS. 17A and 17B).
Given that injury to HSV is associated with decreases in
Niban phosphorylation, this finding indicates that Niban can
be involved in cellular signaling events that regulate the
response to vascular injury and that NiPp can be used to
improve endothelial function in diseased human tissues.

Since NiPp treatment was associated with decreased
phosphorylation of p38 MAPK in RA, a mechanism of NiPp
function can kinase inhibition. Therefore, a kinase profiling
assay was performed to determine the effect of NiPp on the
activity of a panel of kinases in vitro. The top two kinases
inhibited by NiPp were MSK1 and p38 MAPKα. Inhibition
to the p38 MAPKα isoform appeared to be specific as
inhibition by NiPp to the other isoforms (β, δ, and γ) in the
kinaseprofiling screen were only at 5, 3, and 3% respec-
tively. Despite high sequence homology, the isoforms have
difference in tissue expression, upstream kinase activators
and downstream substrates. The p38 MAPKα isoform,
initially identified as a protein that underwent phosphory-
lation in response to endotoxin treatment and hyperosmo-
larity shock, plays a role in endothelial dysfunction in that
inhibition of this isoform leads to improved endothelial
function in animal models of cardiovascular diseases includ-
ing cardiac hypertrophy, balloon injury, salt/fat induced
hypertension and in hypercholesterolemic patients. The
α-isoform is also a key regulator of pro-inflammatory cyto-
kine production and itself can be activated by IL1-β. MSK1,
a downstream kinase of the p38 MAPK activation (FIG. 19),
has complex cell-dependent roles in inflammatory
responses. In endothelial cells, MSK1 promotes CREB
activation in response to TNFα.

Niban gene expression is altered in several cancers and
acute pancreatitis. Niban gene expression is also upregulated
by IL1-β and has been implicated in steroid-responsive
inflammatory responses in asthma. Further analyses of the
STRING database revealed that the candidate targets of
NiPp are involved in in 39 KEGG pathways that are impli-
cated in cancer development, stress responses, and cytoskel-
etal regulation. These data show Niban as a stress response
protein that participates in cellular injury responses.

While p38 MAPK activation plays a role in the response
to injury, subsequent downregulation after injury is neces-
sary to restore cellular homeostasis, uncontrolled p38
MAPK responses can contribute to aberrant downstream
p38 MAPK-dependent signaling. Activation of p38 MAPK
occurs via phosphorylation of the Thr-Gly-Tyr motif by
upstream MKKKs and MKK3/MKK6. Typically, protein
phosphatases interact with kinases to downregulate activa-
tion. More recently, microRNAs were also reported to
regulate p38 MAPK. A number of protein phosphatases have
been identified to carry out this function on p38 MAPK. The
finding that NiPp reduces p38 MAPK phosphorylation and
restores function after vascular injury indicates that Niban
can be an endogenous down-regulator of p38 MAPK that
restores cellular homeostasis after injury. This is consistent
with some of the known functions of Niban as a stress
responsive molecule. Very few endogenous kinase inhibitors
have been identified and characterized to date.

Protein kinase inhibitor (PKI), which inhibits Protein
Kinase A, is an anti-inflammatory and anti-proliferative
protein regulator in endothelial and vascular smooth muscle
cells, respectively. Another endogenous kinase inhibitor, secretoneurin, inhibits Calcium/Calmodulin-Dependent Protein Kinase II and attenuates calcium-dependent arrhythmias as well as playing a critical role in neural vasculature. Thus, while few endogenous kinase inhibitors have been identified, they do exist and phosphorylated Niban may, at least in part, modulate cellular responses via p38 MAPK inhibition.

p38 MAPK has been a prime target for the development of small molecule therapeutics; however, given its central role in many organs, toxicity has been a major limitation due to the crosstalk between different intracellular pathways that p38 MAPK regulates. The investigation and determination that NiPp possesses an isoform-specific inhibitory property to p38 MAPK offers a therapeutic that mimics endogenous signaling, in a tissue specific manner. Moreover, NiPp modulation of the p38 MAPK signaling pathway can attenuate injury responses that occur during traumatic injuries such as surgery, sepsis, or inflammatory diseases. In addition, the unique approach of utilizing a cell permeant peptide analogue of phosphorylated Niban to elucidate the function of this molecule and its role in p38 MAPK signaling cascade is relevant to intact vascular and other tissues where genetic engineering approaches are less optimal due to low cellular turnover.

Example 17. NiPp is a p38MAPKα Inhibitor

The p38 mitogen-activated protein kinase (MAPK) family consist of four isoforms: p38α, p38β, p38γ, and p38δ. In response to extracellular stimuli such as cytokines and stress, p38MAPK is activated by phosphorylation at threonine-180 and tyrosine-182 and phosphorylates downstream mediators such as other kinases and transcription factors. p38MAPK kinase signaling plays an important role in inflammation and other physiological processes and deregulation of these signaling pathways contribute to progression of cardiovascular diseases, inflammatory diseases, chronic pain, and cancer. Specific targeting of p38MAPK can be therapeutic strategies.

The data in FIGS. 7B, 8B, 14A, 14B, 15C, 15D, 19A and 19D show that NiPp is a p38MAPKα inhibitor. Such function can be applied for therapeutic use to treat or prevent inflammatory diseases (sepsis, rheumatoid arthritis, Crohn's disease, asthma, COPD), chronic pain, and cancers.

```
                         SEQUENCES

Human Niban (FAM129A) Protein Sequence (SEQ ID
NO: 75)
MGGSASSQLDEGKCAYIRGKTEAAIKNFSPYYSRQYSVAFCNHVRTEVE
QQRDLTSQFLKTKPPLAPGTILYEAELSQFSEDIKKWKERYVVVKNDYA
VESYENKEAYQRGAAPKCRILPAGGKVLTSEDEYNLLSDRHFPDPLASS
EKENTQPFVVLPKEFPVYLWQPFFRHGYFCFHEAADQKRFSALLSDCVR
HLNHDYMKQMTFEAQAFLEAVQFFRQEKGHYGSWEMITGDEIQILSNLV
MEELLPTLQTDLLPKMKGKKNDRKRTWLGLLEEAYTLVQHQVSEGLSAL
KEECRALTKGLEGTIRSDMDQIVNSKNYLIGKIKAMVAQPAEKSCLESV
QPFLASILEELMGPVSSGFSEVRVLFEKEVNEVSQNFQTTKDSVQLKEH
LDRLMNLPLHSVKMEPCYTKVNLLHERLQDLKSRFRFPHIDLVVQRTQN
YMQELMENAVFTFEQLLSPHLQGEASKTAVAIEKVKLRVLKQYDYDSST
IRKKIFQEALVQITLPTVQKALASTCKPELQKYEQFIFADHTNMIHVEN
VYEEILHQILLDETLKVIKEAAILKKHNLFEDNMALPSESVSSLTDLKP
PTGSNQASPARRASAILPGVLGSETLSNEVFQESEEEKQPEVPSSLAKG
ESLSLPGPSPPPDGTEQVIISRVDDPVVNPVATEDTAGLPGTCSSELEF
GGTLEDEEPAQEEPEPITASGSLKALRKLLTASVEVPVDSAPVMEEDTN
GESHVPQENEEEEEKEPSQAAAIHPDNCEESEVSEREAQPPCPEAHGEE
LGGFPEVGSPASPPASGGLTEEPLGPMEGELPGEACTLTAHEGRGGKCT
EEGDASQQEGCTLGSDPICLSESQVSEEQEEMGGQSSAAQATASVNAEE
IKVARIHECQWVVEDAPNPDVLLSHKDDVKEGEGGQESFPELPSEE
```

Sequences for Niban (also known as FAM129A) homologs can include the following sequences as identified by their accession numbers, for example: Human NP_443198.1; Rat NP_071578.2; Mouse NP_071301.2; Pig, NP_001230148.1; or Dog, XP_537163.2.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

TABLE 1

Composition of polypeptides. Composition of polypeptides consisting of a sequence according to the general formula: X1-X2. Sequences of polypeptides indicated by single-letter amino acid code. (PS) denotes phosphoserine. NiPp2 is a polypeptide containing shortened sequence of X2 of NiPp (SEQ ID NO: 76). NiPp3 is a control polypeptide containing non-phosphorylated sequence of X2 of NiPp (SEQ ID NO: 77). scr3NiPp3 is a control polypeptide containing scrambled sequence of X2 of NiPp (SEQ ID NO: 79).

| Peptides | Sequences | Composition | | |
| --- | --- | --- | --- | --- |
| | | X1 | X2 | |
| NiPp | (SEQ ID NO: 1) YARAAARQARASPAARRA(pS)AILPG | (SEQ ID NO: 22) YARAAARQARA | (SEQ ID NO: 24) SPAARRA(pS)AILPG | |
| NiPp2 | (SEQ ID NO: 76) YARAAARQARAARRA(pS)AILPG | (SEQ ID NO: 22) YARAAARQARA | (SEQ ID NO: 30) ARRA(pS)AILPG | |
| NiPp3 | (SEQ ID NO: 77) YARAAARQARASPAARRASAILPG | (SEQ ID NO: 22) YARAAARQARA | (SEQ ID NO: 78) SPAARRASAILPG | |
| scr3NiPp | (SEQ ID NO: 79) YARAAARQARAAGSPPLA(pS)AIARR | (SEQ ID NO: 22) YARAAARQARA | (SEQ ID NO: 80) AGSPPLA(pS)AIARR | |

We claim:

1. A method for restoring endothelial function, comprising:

administering to a subject in need thereof an effective amount of a polypeptide comprising:

an amino acid sequence according to the general formula X1-X2; wherein

X1 comprises a transduction domain, wherein the transduction domain comprises GRKKRRORRRPPQ (SEQ ID NO:3); AYARAAARQARA (SEQ ID NO:4); DAATATRGRSAASRPTERPRAPARSASRPRRPVE (SEQ ID NO:5); GWTLNSAGYLLGLINLKALAALAKKIL (SEQ ID NO:6); PLSSISRIGDP (SEQ ID NO:7); AAVALLPAVLLALLAP (SEQ ID NO:8); AAVLLPVLLAAP (SEQ ID NO:9); VTVLALGALAGVGVG (SEQ ID NO:10); GALFLGWLGAAGSTMGAWSQP (SEQ ID NO:11); GWTLNSAGYLLGLINLKALAALAKKIL (SEQ ID NO:12); KLALKLALKALKAALKLA (SEQ ID NO:13); KETWWETWWTEWSQPKKKRKV (SEQ ID NO:14); KAFAKLAARLYRKAGC (SEQ ID NO:15); KAFAKLAARLYRAAGC (SEQ ID NO:16); AAFAKLAARLYRKAGC (SEQ ID NO:17); KAFAALAARLYRKAGC (SEQ ID NO:18); KAFAKLAAQLYRKAGC (SEQ ID NO:19), AGGGGYGRKKRRORRR (SEQ ID NO:20); YGRKKRRORRR (SEQ ID NO:21); YARAAARQARA (SEQ ID NO:22); or LTVK (SEQ ID NO:23); and X2 comprises a polypeptide capable of restoring endothelial function;

wherein X2 is selected from SPAARRA (pS) AILPG (SEQ ID NO:24); SPARRA (pS) AILPG (SEQ ID NO:25); SPAARRV (pS) AILPG (SEQ ID NO:26); SPARRV (pS) AILPG (SEQ ID NO:27); SPAARGA (pS) AILPG (SEQ ID NO:28); SPARGA (pS) AILPG (SEQ ID NO:29); ARRA (pS) AILPG (SEQ ID NO:30); ARRV (pS) AILPG (SEQ ID NO:31); ARGA (pS) AILPG (SEQ ID NO:32); or SPARRA (pS) ALLPG (SEQ ID NO:74);

wherein X2 includes Z3; and wherein Z3 is selected from a phosphoserine or a phosphoserine analog.

2. The method of claim 1, wherein X2 comprises SPAARRA (pS) AILPG (SEQ ID NO:24).

3. The method of claim 1, wherein X1 comprises YARAAARQARA (SEQ ID NO:22).

4. The method of claim 1, wherein Z3 comprises a phosphoserine.

5. The method of claim 1, wherein Z3 comprises a phosphoserine analog.

6. The method of claim 1, wherein the polypeptide comprises the sequence (SEQ ID NO: 1)
YARAAARQARASPAARRA(pS)AILPG.

* * * * *

SEQUENCE LISTING

<160> NUMBER OF SEQ ID NOS: 80

<210> SEQ ID NO 1
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (19)..(19)
<223> OTHER INFORMATION: S is phosphoserine

<400> SEQUENCE: 1

Tyr Ala Arg Ala Ala Ala Arg Gln Ala Arg Ala Ser Pro Ala Ala Arg
1               5                   10                  15

Arg Ala Ser Ala Ile Leu Pro Gly
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (15)..(15)
<223> OTHER INFORMATION: S is phosphoserine

<400> SEQUENCE: 2

Tyr Ala Arg Ala Ala Ala Arg Gln Ala Arg Ala Ala Pro Ala Ser Ala
1               5                   10                  15

Arg Ile Ala Leu Pro Gly Ser Arg
            20

<210> SEQ ID NO 3
<211> LENGTH: 13
<212> TYPE: PRT
<213> ORGANISM: Artificial Sequence
<220> FEATURE:
<223> OTHER INFORMATION: Synthetic construct

<400> SEQUENCE: 3

Gly Arg Lys Lys Arg Arg Gln Arg Arg Arg Pro Pro Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic construct

<400> SEQUENCE: 4

Ala Tyr Ala Arg Ala Ala Ala Arg Gln Ala Arg Ala
1               5                   10

<210> SEQ ID NO 5
<211> LENGTH: 34
<212> TYPE: PRT
<213> ORGANISM: Artificial Sequence
<220> FEATURE:
<223> OTHER INFORMATION: Synthetic construct

<400> SEQUENCE: 5

Asp Ala Ala Thr Ala Thr Arg Gly Arg Ser Ala Ala Ser Arg Pro Thr

```
1               5               10              15

Glu Arg Pro Arg Ala Pro Ala Arg Ser Ala Ser Arg Pro Arg Arg Pro
            20              25              30

Val Glu

<210> SEQ ID NO 6
<211> LENGTH: 27
<212> TYPE: PRT
<213> ORGANISM: Artificial Sequence
<220> FEATURE:
<223> OTHER INFORMATION: Synthetic construct

<400> SEQUENCE: 6

Gly Trp Thr Leu Asn Ser Ala Gly Tyr Leu Leu Gly Leu Ile Asn Leu
1               5               10              15

Lys Ala Leu Ala Ala Leu Ala Lys Lys Ile Leu
            20              25

<210> SEQ ID NO 7
<211> LENGTH: 11
<212> TYPE: PRT
<213> ORGANISM: Artificial Sequence
<220> FEATURE:
<223> OTHER INFORMATION: Synthetic construct

<400> SEQUENCE: 7

Pro Leu Ser Ser Ile Ser Arg Ile Gly Asp Pro
1               5               10

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8

Ala Ala Val Ala Leu Leu Pro Ala Val Leu Leu Ala Leu Leu Ala Pro
1               5               10              15

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Ala Ala Val Leu Leu Pro Val Leu Leu Ala Ala Pro
1               5               10

<210> SEQ ID NO 10
<211> LENGTH: 15
<212> TYPE: PRT
<213> ORGANISM: Artificial Sequence
<220> FEATURE:
<223> OTHER INFORMATION: Synthetic construct

<400> SEQUENCE: 10

Val Thr Val Leu Ala Leu Gly Ala Leu Ala Gly Val Gly Val Gly
1               5               10              15

<210> SEQ ID NO 11
<211> LENGTH: 21
<212> TYPE: PRT
```

```
<213> ORGANISM: Artificial Sequence
<220> FEATURE:
<223> OTHER INFORMATION: Synthetic construct

<400> SEQUENCE: 11

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 12
<211> LENGTH: 27
<212> TYPE: PRT
<213> ORGANISM: Artificial Sequence
<220> FEATURE:
<223> OTHER INFORMATION: Synthetic construct

<400> SEQUENCE: 12

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 13
<211> LENGTH: 18
<212> TYPE: PRT
<213> ORGANISM: Artificial Sequence
<220> FEATURE:
<223> OTHER INFORMATION: Synthetic construct

<400> SEQUENCE: 13

Lys Leu Ala Leu Lys Leu Ala Leu Lys Ala Leu Lys Ala Ala Leu Lys
1               5                   10                  15

Leu Ala

<210> SEQ ID NO 14
<211> LENGTH: 21
<212> TYPE: PRT
<213> ORGANISM: Artificial Sequence
<220> FEATURE:
<223> OTHER INFORMATION: Synthetic construct

<400> SEQUENCE: 14

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 15
<211> LENGTH: 16
<212> TYPE: PRT
<213> ORGANISM: Artificial Sequence
<220> FEATURE:
<223> OTHER INFORMATION: Synthetic construct

<400> SEQUENCE: 15

Lys Ala Phe Ala Lys Leu Ala Ala Arg Leu Tyr Arg Lys Ala Gly Cys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic construct
```

```
<400> SEQUENCE: 16

Lys Ala Phe Ala Lys Leu Ala Ala Arg Leu Tyr Arg Ala Ala Gly Cys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Ala Ala Phe Ala Lys Leu Ala Ala Arg Leu Tyr Arg Lys Ala Gly Cys
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic construct

<400> SEQUENCE: 18

Lys Ala Phe Ala Ala Leu Ala Ala Arg Leu Tyr Arg Lys Ala Gly Cys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic construct

<400> SEQUENCE: 19

Lys Ala Phe Ala Lys Leu Ala Ala Gln Leu Tyr Arg Lys Ala Gly Cys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic construct

<400> SEQUENCE: 20

Ala Gly Gly Gly Gly Tyr Gly Arg Lys Lys Arg Arg Gln Arg Arg Arg
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Synthetic construct

<400> SEQUENCE: 21

Tyr Gly Arg Lys Lys Arg Arg Gln Arg Arg Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic construct
```

```
<400> SEQUENCE: 22

Tyr Ala Arg Ala Ala Ala Arg Gln Ala Arg Ala
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Synthetic construct

<400> SEQUENCE: 23

Leu Thr Val Lys
1

<210> SEQ ID NO 24
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: S is phosphoserine

<400> SEQUENCE: 24

Ser Pro Ala Ala Arg Arg Ala Ser Ala Ile Leu Pro Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: S is phosphoserine

<400> SEQUENCE: 25

Ser Pro Ala Arg Arg Ala Ser Ala Ile Leu Pro Gly
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: S is phosphoserine

<400> SEQUENCE: 26

Ser Pro Ala Ala Arg Arg Val Ser Ala Ile Leu Pro Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
```

<223> OTHER INFORMATION: S is phosphoserine

<400> SEQUENCE: 27

Ser Pro Ala Arg Arg Val Ser Ala Ile Leu Pro Gly
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: S is phosphoserine

<400> SEQUENCE: 28

Ser Pro Ala Ala Arg Gly Ala Ser Ala Ile Leu Pro Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: S is phosphoserine

<400> SEQUENCE: 29

Ser Pro Ala Arg Gly Ala Ser Ala Ile Leu Pro Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: S is phosphoserine

<400> SEQUENCE: 30

Ala Arg Arg Ala Ser Ala Ile Leu Pro Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: S is phosphoserine

<400> SEQUENCE: 31

Ala Arg Arg Val Ser Ala Ile Leu Pro Gly
1               5                   10

<210> SEQ ID NO 32
<211> LENGTH: 10
<212> TYPE: PRT

-continued

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: S is phosphoserine

<400> SEQUENCE: 32

Ala Arg Gly Ala Ser Ala Ile Leu Pro Gly
1               5                   10

<210> SEQ ID NO 33
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 33

Gly Arg Lys Lys Arg Arg Gln Arg Arg Pro Pro Gln Ser Pro Ala
1               5                   10                  15

Ala Arg Arg Ala Ser Ala Ile Leu Pro Gly
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (20)..(20)
<223> OTHER INFORMATION: S is phosphoserine

<400> SEQUENCE: 34

Ala Tyr Ala Arg Ala Ala Ala Arg Gln Ala Arg Ala Ser Pro Ala Ala
1               5                   10                  15

Arg Arg Ala Ser Ala Ile Leu Pro Gly
            20                  25

<210> SEQ ID NO 35
<211> LENGTH: 47
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (42)..(42)
<223> OTHER INFORMATION: S is phosphoserine

<400> SEQUENCE: 35

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu Ser Pro Ala Ala Arg Arg Ala Ser Ala Ile Leu Pro Gly
            35                  40                  45

<210> SEQ ID NO 36
<211> LENGTH: 40
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (35)..(35)
<223> OTHER INFORMATION: S is phosphoserine

<400> SEQUENCE: 36

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu Ser Pro Ala Ala Arg
            20                  25                  30

Arg Ala Ser Ala Ile Leu Pro Gly
        35                  40

<210> SEQ ID NO 37
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (19)..(19)
<223> OTHER INFORMATION: S is phosphoserine

<400> SEQUENCE: 37

Pro Leu Ser Ser Ile Ser Arg Ile Gly Asp Pro Ser Pro Ala Ala Arg
1               5                   10                  15

Arg Ala Ser Ala Ile Leu Pro Gly
            20

<210> SEQ ID NO 38
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: S is phosphoserine

<400> SEQUENCE: 38

Ala Ala Val Ala Leu Leu Pro Ala Val Leu Leu Ala Leu Leu Ala Pro
1               5                   10                  15

Ser Pro Ala Ala Arg Arg Ala Ser Ala Ile Leu Pro Gly
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (19)..(19)
<223> OTHER INFORMATION: S is phosphoserine

<400> SEQUENCE: 39

Ala Ala Val Leu Leu Pro Val Leu Leu Ala Ala Pro Ser Pro Ala Ala
1               5                   10                  15

Arg Arg Ala Ser Ala Ile Leu Pro Gly
            20                  25
```

```
<210> SEQ ID NO 40
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (23)..(23)
<223> OTHER INFORMATION: S is phosphoserine

<400> SEQUENCE: 40

Val Thr Val Leu Ala Leu Gly Ala Leu Ala Gly Val Gly Val Gly Ser
1               5                   10                  15

Pro Ala Ala Arg Arg Ala Ser Ala Ile Leu Pro Gly
            20                  25

<210> SEQ ID NO 41
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: S is phosphoserine

<400> SEQUENCE: 41

Gly Ala Leu Phe Leu Gly Trp Leu Gly Ala Ala Gly Ser Thr Met Gly
1               5                   10                  15

Ala Trp Ser Gln Pro Ser Pro Ala Ala Arg Arg Ala Ser Ala Ile Leu
            20                  25                  30

Pro Gly

<210> SEQ ID NO 42
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (35)..(35)
<223> OTHER INFORMATION: S is phosphoserine

<400> SEQUENCE: 42

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu Ser Pro Ala Ala Arg
            20                  25                  30

Arg Ala Ser Ala Ile Leu Pro Gly
            35                  40

<210> SEQ ID NO 43
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(26)
<223> OTHER INFORMATION: S is phosphoserine

<400> SEQUENCE: 43
```

```
Lys Leu Ala Leu Lys Leu Ala Leu Lys Ala Leu Lys Ala Ala Leu Lys
1               5                   10                  15

Leu Ala Ser Pro Ala Ala Arg Arg Ala Ser Ala Ile Leu Pro Gly
            20                  25                  30

<210> SEQ ID NO 44
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(29)
<223> OTHER INFORMATION: S is phosphoserine

<400> SEQUENCE: 44

Lys Glu Thr Trp Trp Glu Thr Trp Trp Thr Glu Trp Ser Gln Pro Lys
1               5                   10                  15

Lys Lys Arg Lys Val Ser Pro Ala Ala Arg Arg Ala Ser Ala Ile Leu
            20                  25                  30

Pro Gly

<210> SEQ ID NO 45
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: S is phosphoserine

<400> SEQUENCE: 45

Lys Ala Phe Ala Lys Leu Ala Ala Arg Leu Tyr Arg Lys Ala Gly Cys
1               5                   10                  15

Ser Pro Ala Ala Arg Arg Ala Ser Ala Ile Leu Pro Gly
            20                  25

<210> SEQ ID NO 46
<211> LENGTH: 29
<212> TYPE: PRT
<213> ORGANISM: Artificial Sequence
<220> FEATURE:
<223> OTHER INFORMATION: Synthetic contsruct
<220> FEATURE:
<221> NAME/KEY: MISC_FEATURE
<222> LOCATION: (24)..(24)
<223> OTHER INFORMATION: S is phosphoserine

<400> SEQUENCE: 46

Lys Ala Phe Ala Lys Leu Ala Ala Arg Leu Tyr Arg Ala Ala Gly Cys
1               5                   10                  15

Ser Pro Ala Ala Arg Arg Ala Ser Ala Ile Leu Pro Gly
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
```

<223> OTHER INFORMATION: S is phosphoserine

<400> SEQUENCE: 47

Ala Ala Phe Ala Lys Leu Ala Ala Arg Leu Tyr Arg Lys Ala Gly Cys
1               5                   10                  15

Ser Pro Ala Ala Arg Arg Ala Ser Ala Ile Leu Pro Gly
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: S is phosphoserine

<400> SEQUENCE: 48

Lys Ala Phe Ala Ala Leu Ala Ala Arg Leu Tyr Arg Lys Ala Gly Cys
1               5                   10                  15

Ser Pro Ala Ala Arg Arg Ala Ser Ala Ile Leu Pro Gly
            20                  25

<210> SEQ ID NO 49
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: S is phosphoserine

<400> SEQUENCE: 49

Lys Ala Phe Ala Lys Leu Ala Ala Gln Leu Tyr Arg Lys Ala Gly Cys
1               5                   10                  15

Ser Pro Ala Ala Arg Arg Ala Ser Ala Ile Leu Pro Gly
            20                  25

<210> SEQ ID NO 50
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: S is phosphoserine

<400> SEQUENCE: 50

Ala Gly Gly Gly Gly Tyr Gly Arg Lys Lys Arg Arg Gln Arg Arg
1               5                   10                  15

Ser Pro Ala Ala Arg Arg Ala Ser Ala Ile Leu Pro Gly
            20                  25

<210> SEQ ID NO 51
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (19)..(19)
<223> OTHER INFORMATION: S is phosphoserine

<400> SEQUENCE: 51

Tyr Gly Arg Lys Lys Arg Arg Gln Arg Arg Ser Pro Ala Ala Arg
1               5                   10                  15

Arg Ala Ser Ala Ile Leu Pro Gly
            20

<210> SEQ ID NO 52
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (12)..(12)
<223> OTHER INFORMATION: S is phosphoserine

<400> SEQUENCE: 52

Leu Thr Val Lys Ser Pro Ala Ala Arg Arg Ala Ser Ala Ile Leu Pro
1               5                   10                  15

Gly

<210> SEQ ID NO 53
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (18)..(18)
<223> OTHER INFORMATION: S is phosphoserine

<400> SEQUENCE: 53

Gly Arg Lys Lys Arg Arg Gln Arg Arg Arg Pro Pro Gln Ala Arg Arg
1               5                   10                  15

Ala Ser Ala Ile Leu Pro Gly
            20

<210> SEQ ID NO 54
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (17)..(17)
<223> OTHER INFORMATION: S is phosphoserine

<400> SEQUENCE: 54

Ala Tyr Ala Arg Ala Ala Ala Arg Gln Ala Arg Ala Ala Arg Arg Ala
1               5                   10                  15

Ser Ala Ile Leu Pro Gly
            20

<210> SEQ ID NO 55
<211> LENGTH: 44
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE -continued

```
<222> LOCATION: (39)..(39)
<223> OTHER INFORMATION: S is phosphoserine

<400> SEQUENCE: 55

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu Ala Arg Arg Ala Ser Ala Ile Leu Pro Gly
        35                  40

<210> SEQ ID NO 56
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (32)..(32)
<223> OTHER INFORMATION: S is phosphoserine

<400> SEQUENCE: 56

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu Ala Arg Arg Ala Ser
            20                  25                  30

Ala Ile Leu Pro Gly
        35

<210> SEQ ID NO 57
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: S is phosphoserine

<400> SEQUENCE: 57

Pro Leu Ser Ser Ile Ser Arg Ile Gly Asp Pro Ala Arg Arg Ala Ser
1               5                   10                  15

Ala Ile Leu Pro Gly
            20

<210> SEQ ID NO 58
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 58

Ala Ala Val Ala Leu Leu Pro Ala Val Leu Leu Ala Leu Leu Ala Pro
1               5                   10                  15

Ala Arg Arg Ala Ser Ala Ile Leu Pro Gly
            20                  25

<210> SEQ ID NO 59
```

```
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (17)..(17)
<223> OTHER INFORMATION: S is phosphoserine

<400> SEQUENCE: 59

Ala Ala Val Leu Leu Pro Val Leu Leu Ala Ala Pro Ala Arg Arg Ala
1               5                   10                  15

Ser Ala Ile Leu Pro Gly
            20

<210> SEQ ID NO 60
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (20)..(20)
<223> OTHER INFORMATION: S is phosphoserine

<400> SEQUENCE: 60

Val Thr Val Leu Ala Leu Gly Ala Leu Ala Gly Val Gly Val Gly Ala
1               5                   10                  15

Arg Arg Ala Ser Ala Ile Leu Pro Gly
            20                  25

<210> SEQ ID NO 61
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(26)
<223> OTHER INFORMATION: S is phosphoserine

<400> SEQUENCE: 61

Gly Ala Leu Phe Leu Gly Trp Leu Gly Ala Ala Gly Ser Thr Met Gly
1               5                   10                  15

Ala Trp Ser Gln Pro Ala Arg Arg Ala Ser Ala Ile Leu Pro Gly
            20                  25                  30

<210> SEQ ID NO 62
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (32)..(32)
<223> OTHER INFORMATION: S is phosphoserine

<400> SEQUENCE: 62

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu Ala Arg Arg Ala Ser
            20                  25                  30

Ala Ile Leu Pro Gly
```

35

```
<210> SEQ ID NO 63
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (23)..(23)
<223> OTHER INFORMATION: S is phosphoserine

<400> SEQUENCE: 63

Lys Leu Ala Leu Lys Leu Ala Leu Lys Ala Leu Lys Ala Ala Leu Lys
1               5                   10                  15

Leu Ala Ala Arg Arg Ala Ser Ala Ile Leu Pro Gly
            20                  25

<210> SEQ ID NO 64
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(26)
<223> OTHER INFORMATION: S is phosphoserine

<400> SEQUENCE: 64

Lys Glu Thr Trp Trp Glu Thr Trp Trp Thr Glu Trp Ser Gln Pro Lys
1               5                   10                  15

Lys Lys Arg Lys Val Ala Arg Arg Ala Ser Ala Ile Leu Pro Gly
            20                  25                  30

<210> SEQ ID NO 65
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 65

Lys Ala Phe Ala Lys Leu Ala Ala Arg Leu Tyr Arg Lys Ala Gly Cys
1               5                   10                  15

Ala Arg Arg Ala Ser Ala Ile Leu Pro Gly
            20                  25

<210> SEQ ID NO 66
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 66

Lys Ala Phe Ala Lys Leu Ala Ala Arg Leu Tyr Arg Ala Ala Gly Cys
1               5                   10                  15
```

```
Ala Arg Arg Ala Ser Ala Ile Leu Pro Gly
            20                  25

<210> SEQ ID NO 67
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 67

Ala Ala Phe Ala Lys Leu Ala Ala Arg Leu Tyr Arg Lys Ala Gly Cys
1               5                   10                  15

Ala Arg Arg Ala Ser Ala Ile Leu Pro Gly
            20                  25

<210> SEQ ID NO 68
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 68

Lys Ala Phe Ala Ala Leu Ala Ala Arg Leu Tyr Arg Lys Ala Gly Cys
1               5                   10                  15

Ala Arg Arg Ala Ser Ala Ile Leu Pro Gly
            20                  25

<210> SEQ ID NO 69
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 69

Lys Ala Phe Ala Lys Leu Ala Ala Gln Leu Tyr Arg Lys Ala Gly Cys
1               5                   10                  15

Ala Arg Arg Ala Ser Ala Ile Leu Pro Gly
            20                  25

<210> SEQ ID NO 70
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (21)..(21)
<223> OTHER INFORMATION: S is phosphoserine

<400> SEQUENCE: 70

Ala Gly Gly Gly Gly Tyr Gly Arg Lys Lys Arg Arg Gln Arg Arg Arg
1               5                   10                  15
```

```
Ala Arg Arg Ala Ser Ala Ile Leu Pro Gly
            20                  25

<210> SEQ ID NO 71
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: S is phosphoserine

<400> SEQUENCE: 71

Tyr Gly Arg Lys Lys Arg Arg Gln Arg Arg Arg Ala Arg Arg Ala Ser
1               5                   10                  15

Ala Ile Leu Pro Gly
            20

<210> SEQ ID NO 72
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: S is phosphoserine

<400> SEQUENCE: 72

Leu Thr Val Lys Ala Arg Arg Ala Ser Ala Ile Leu Pro Gly
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: S is phosphoserine

<400> SEQUENCE: 73

Ala Pro Ala Ser Ala Arg Ile Ala Leu Pro Gly Ser Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: S is phosphoserine

<400> SEQUENCE: 74

Ser Pro Ala Arg Arg Ala Ser Ala Leu Leu Pro Gly
1               5                   10

<210> SEQ ID NO 75
<211> LENGTH: 928
<212> TYPE: PRT
```

```
<213> ORGANISM: Artificial Sequence
<220> FEATURE:
<223> OTHER INFORMATION: Synthetic construct

<400> SEQUENCE: 75

Met Gly Gly Ser Ala Ser Ser Gln Leu Asp Glu Gly Lys Cys Ala Tyr
1               5                   10                  15

Ile Arg Gly Lys Thr Glu Ala Ala Ile Lys Asn Phe Ser Pro Tyr Tyr
                20                  25                  30

Ser Arg Gln Tyr Ser Val Ala Phe Cys Asn His Val Arg Thr Glu Val
            35                  40                  45

Glu Gln Gln Arg Asp Leu Thr Ser Gln Phe Leu Lys Thr Lys Pro Pro
    50                  55                  60

Leu Ala Pro Gly Thr Ile Leu Tyr Glu Ala Glu Leu Ser Gln Phe Ser
65                  70                  75                  80

Glu Asp Ile Lys Lys Trp Lys Glu Arg Tyr Val Val Val Lys Asn Asp
                85                  90                  95

Tyr Ala Val Glu Ser Tyr Glu Asn Lys Glu Ala Tyr Gln Arg Gly Ala
            100                 105                 110

Ala Pro Lys Cys Arg Ile Leu Pro Ala Gly Gly Lys Val Leu Thr Ser
            115                 120                 125

Glu Asp Glu Tyr Asn Leu Leu Ser Asp Arg His Phe Pro Asp Pro Leu
    130                 135                 140

Ala Ser Ser Glu Lys Glu Asn Thr Gln Pro Phe Val Val Leu Pro Lys
145                 150                 155                 160

Glu Phe Pro Val Tyr Leu Trp Gln Pro Phe Phe Arg His Gly Tyr Phe
                165                 170                 175

Cys Phe His Glu Ala Ala Asp Gln Lys Arg Phe Ser Ala Leu Leu Ser
            180                 185                 190

Asp Cys Val Arg His Leu Asn His Asp Tyr Met Lys Gln Met Thr Phe
            195                 200                 205

Glu Ala Gln Ala Phe Leu Glu Ala Val Gln Phe Phe Arg Gln Glu Lys
    210                 215                 220

Gly His Tyr Gly Ser Trp Glu Met Ile Thr Gly Asp Glu Ile Gln Ile
225                 230                 235                 240

Leu Ser Asn Leu Val Met Glu Glu Leu Leu Pro Thr Leu Gln Thr Asp
                245                 250                 255

Leu Leu Pro Lys Met Lys Gly Lys Lys Asn Asp Arg Lys Arg Thr Trp
                260                 265                 270

Leu Gly Leu Leu Glu Glu Ala Tyr Thr Leu Val Gln His Gln Val Ser
            275                 280                 285

Glu Gly Leu Ser Ala Leu Lys Glu Glu Cys Arg Ala Leu Thr Lys Gly
    290                 295                 300

Leu Glu Gly Thr Ile Arg Ser Asp Met Asp Gln Ile Val Asn Ser Lys
305                 310                 315                 320

Asn Tyr Leu Ile Gly Lys Ile Lys Ala Met Val Ala Gln Pro Ala Glu
                325                 330                 335

Lys Ser Cys Leu Glu Ser Val Gln Pro Phe Leu Ala Ser Ile Leu Glu
            340                 345                 350

Glu Leu Met Gly Pro Val Ser Ser Gly Phe Ser Glu Val Arg Val Leu
            355                 360                 365

Phe Glu Lys Glu Val Asn Glu Val Ser Gln Asn Phe Gln Thr Thr Lys
    370                 375                 380

Asp Ser Val Gln Leu Lys Glu His Leu Asp Arg Leu Met Asn Leu Pro
```

-continued

```
385               390               395               400

Leu His Ser Val Lys Met Glu Pro Cys Tyr Thr Lys Val Asn Leu Leu
            405               410               415

His Glu Arg Leu Gln Asp Leu Lys Ser Arg Phe Arg Phe Pro His Ile
            420               425               430

Asp Leu Val Val Gln Arg Thr Gln Asn Tyr Met Gln Glu Leu Met Glu
            435               440               445

Asn Ala Val Phe Thr Phe Glu Gln Leu Leu Ser Pro His Leu Gln Gly
      450               455               460

Glu Ala Ser Lys Thr Ala Val Ala Ile Glu Lys Val Lys Leu Arg Val
465               470               475               480

Leu Lys Gln Tyr Asp Tyr Asp Ser Ser Thr Ile Arg Lys Lys Ile Phe
                  485               490               495

Gln Glu Ala Leu Val Gln Ile Thr Leu Pro Thr Val Gln Lys Ala Leu
            500               505               510

Ala Ser Thr Cys Lys Pro Glu Leu Gln Lys Tyr Glu Gln Phe Ile Phe
            515               520               525

Ala Asp His Thr Asn Met Ile His Val Glu Asn Val Tyr Glu Glu Ile
      530               535               540

Leu His Gln Ile Leu Leu Asp Glu Thr Leu Lys Val Ile Lys Glu Ala
545               550               555               560

Ala Ile Leu Lys Lys His Asn Leu Phe Glu Asp Asn Met Ala Leu Pro
                  565               570               575

Ser Glu Ser Val Ser Ser Leu Thr Asp Leu Lys Pro Pro Thr Gly Ser
            580               585               590

Asn Gln Ala Ser Pro Ala Arg Arg Ala Ser Ala Ile Leu Pro Gly Val
            595               600               605

Leu Gly Ser Glu Thr Leu Ser Asn Glu Val Phe Gln Glu Ser Glu Glu
      610               615               620

Glu Lys Gln Pro Glu Val Pro Ser Ser Leu Ala Lys Gly Glu Ser Leu
625               630               635               640

Ser Leu Pro Gly Pro Ser Pro Pro Asp Gly Thr Glu Gln Val Ile
            645               650               655

Ile Ser Arg Val Asp Asp Pro Val Val Asn Pro Val Ala Thr Glu Asp
            660               665               670

Thr Ala Gly Leu Pro Gly Thr Cys Ser Ser Glu Leu Glu Phe Gly Gly
            675               680               685

Thr Leu Glu Asp Glu Glu Pro Ala Gln Glu Glu Pro Glu Pro Ile Thr
      690               695               700

Ala Ser Gly Ser Leu Lys Ala Leu Arg Lys Leu Leu Thr Ala Ser Val
705               710               715               720

Glu Val Pro Val Asp Ser Ala Pro Val Met Glu Glu Asp Thr Asn Gly
            725               730               735

Glu Ser His Val Pro Gln Glu Asn Glu Glu Glu Glu Lys Glu Pro
            740               745               750

Ser Gln Ala Ala Ala Ile His Pro Asp Asn Cys Glu Glu Ser Glu Val
            755               760               765

Ser Glu Arg Glu Ala Gln Pro Pro Cys Pro Glu Ala His Gly Glu Glu
            770               775               780

Leu Gly Gly Phe Pro Glu Val Gly Ser Pro Ala Ser Pro Pro Ala Ser
785               790               795               800

Gly Gly Leu Thr Glu Glu Pro Leu Gly Pro Met Glu Gly Glu Leu Pro
            805               810               815
```

```
Gly Glu Ala Cys Thr Leu Thr Ala His Glu Gly Arg Gly Gly Lys Cys
        820                 825                 830

Thr Glu Glu Gly Asp Ala Ser Gln Gln Glu Gly Cys Thr Leu Gly Ser
        835                 840                 845

Asp Pro Ile Cys Leu Ser Glu Ser Gln Val Ser Glu Glu Gln Glu Glu
        850                 855                 860

Met Gly Gly Gln Ser Ser Ala Ala Gln Ala Thr Ala Ser Val Asn Ala
865                 870                 875                 880

Glu Glu Ile Lys Val Ala Arg Ile His Glu Cys Gln Trp Val Val Glu
                885                 890                 895

Asp Ala Pro Asn Pro Asp Val Leu Leu Ser His Lys Asp Asp Val Lys
                900                 905                 910

Glu Gly Glu Gly Gly Gln Glu Ser Phe Pro Glu Leu Pro Ser Glu Glu
        915                 920                 925

<210> SEQ ID NO 76
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: S is phosphoserine

<400> SEQUENCE: 76

Tyr Ala Arg Ala Ala Ala Arg Gln Ala Arg Ala Ala Arg Arg Ala Ser
1               5                   10                  15

Ala Ile Leu Pro Gly
            20

<210> SEQ ID NO 77
<211> LENGTH: 24
<212> TYPE: PRT
<213> ORGANISM: Artificial Sequence
<220> FEATURE:
<223> OTHER INFORMATION: Synthetic construct

<400> SEQUENCE: 77

Tyr Ala Arg Ala Ala Ala Arg Gln Ala Arg Ala Ser Pro Ala Ala Arg
1               5                   10                  15

Arg Ala Ser Ala Ile Leu Pro Gly
            20

<210> SEQ ID NO 78
<211> LENGTH: 13
<212> TYPE: PRT
<213> ORGANISM: Artificial Sequence
<220> FEATURE:
<223> OTHER INFORMATION: Synthetic construct

<400> SEQUENCE: 78

Ser Pro Ala Ala Arg Arg Ala Ser Ala Ile Leu Pro Gly
1               5                   10

<210> SEQ ID NO 79
<211> LENGTH: 24
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (19)..(19)
<223> OTHER INFORMATION: S is phosphoserine

<400> SEQUENCE: 79

Tyr Ala Arg Ala Ala Ala Arg Gln Ala Arg Ala Ala Gly Ser Pro Pro
1               5                   10                  15

Leu Ala Ser Ala Ile Ala Arg Arg
            20

<210> SEQ ID NO 80
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: S is phosphoserine

<400> SEQUENCE: 80

Ala Gly Ser Pro Pro Leu Ala Ser Ala Ile Ala Arg Arg
1               5                   10
```